United States Patent
Nichols

(10) Patent No.: US 12,359,178 B2
(45) Date of Patent: *Jul. 15, 2025

(54) METHODS AND COMPOSITIONS FOR TREATMENT OF HUNTER SYNDROME COMPRISING IDURONATE-2-SULFATASE

(71) Applicant: Takeda Pharmaceutical Company Limited, Osaka (JP)

(72) Inventor: Dave Nichols, Lexington, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/645,049

(22) Filed: Apr. 24, 2024

(65) Prior Publication Data

US 2024/0401010 A1  Dec. 5, 2024

Related U.S. Application Data

(60) Continuation of application No. 18/052,442, filed on Nov. 3, 2022, now abandoned, which is a continuation of application No. 17/092,034, filed on Nov. 6, 2020, now Pat. No. 11,530,393, which is a continuation of application No. 16/417,440, filed on May 20, 2019, now abandoned, which is a division of application No. 15/279,018, filed on Sep. 28, 2016, now Pat. No. 10,344,270, which is a division of application No. 14/673,607, filed on Mar. 30, 2015, now Pat. No. 9,492,511, which is a division of application No. 13/829,706, filed on Mar. 14, 2013, now Pat. No. 9,051,556.

(60) Provisional application No. 61/666,733, filed on Jun. 29, 2012.

(51) Int. Cl.
*C12N 9/16* (2006.01)
*A61K 38/46* (2006.01)

(52) U.S. Cl.
CPC .............. *C12N 9/16* (2013.01); *A61K 38/465* (2013.01); *C12Y 301/06013* (2013.01)

(58) Field of Classification Search
None
See application file for complete search history.

(56) References Cited

U.S. PATENT DOCUMENTS

| | | | |
|---|---|---|---|
| 5,310,646 A | 5/1994 | Whitley | |
| 5,728,381 A | 3/1998 | Wilson et al. | |
| 6,096,555 A | 8/2000 | Hermentin et al. | |
| 6,153,188 A | 11/2000 | Wilson et al. | |
| 6,506,598 B1 | 1/2003 | Andersen et al. | |
| 6,890,736 B1 | 5/2005 | Reddy et al. | |
| 7,083,793 B2 | 8/2006 | Fraser | |
| 7,282,209 B2 | 10/2007 | Fraser | |
| 7,285,398 B2 | 10/2007 | Fraser | |
| 7,323,553 B2 | 1/2008 | Fahrner et al. | |
| 7,368,531 B2 | 5/2008 | Rosen et al. | |
| 7,541,164 B2 | 6/2009 | Schilling et al. | |
| 7,691,611 B2 | 4/2010 | Weber et al. | |
| 8,128,925 B2 | 3/2012 | Vellard et al. | |
| 8,198,084 B2 | 6/2012 | Gorfien et al. | |
| 8,227,212 B2 | 7/2012 | Von et al. | |
| 9,051,556 B2 | 6/2015 | Nichols | |
| 9,150,841 B2 | 10/2015 | Boldog et al. | |
| 9,206,402 B2 | 12/2015 | Jin et al. | |
| 9,492,511 B2 | 11/2016 | Nichols | |
| 10,344,270 B2 | 7/2019 | Nichols | |
| 11,530,393 B2 * | 12/2022 | Nichols | A61K 38/465 |
| 2002/0106358 A1 | 8/2002 | Hopwood et al. | |
| 2003/0229212 A1 | 12/2003 | Fahrner et al. | |
| 2004/0229250 A1 | 11/2004 | Figura et al. | |
| 2005/0019859 A1 | 1/2005 | Schilling et al. | |
| 2005/0019914 A1 | 1/2005 | Staerk et al. | |
| 2006/0148074 A1 | 7/2006 | Gorfien et al. | |
| 2009/0186011 A1 | 7/2009 | Vellard et al. | |
| 2010/0190210 A1 | 7/2010 | Arunakumari et al. | |
| 2011/0318323 A1 | 12/2011 | Zhu et al. | |
| 2012/0189605 A1 | 7/2012 | Koppaka et al. | |
| 2013/0028881 A1 | 1/2013 | Von et al. | |
| 2013/0195888 A1 | 8/2013 | Wang et al. | |
| 2014/0004096 A1 | 1/2014 | Nichols | |
| 2014/0004097 A1 | 1/2014 | Zhang et al. | |
| 2014/0004593 A1 | 1/2014 | Boldog et al. | |
| 2014/0242059 A1 | 8/2014 | Jin et al. | |
| 2015/0313972 A1 | 11/2015 | Nichols | |

(Continued)

FOREIGN PATENT DOCUMENTS

| | | |
|---|---|---|
| CA | 2839674 A1 | 12/2012 |
| EA | 201490149 A1 | 9/2014 |
| JP | H10500939 A | 1/1998 |

(Continued)

OTHER PUBLICATIONS

U.S. Appl. No. 61/500,994, filed Jun. 24, 2011, Jin et al.
U.S. Appl. No. 61/618,638, filed Mar. 30, 2012, Xie et al.
U.S. Appl. No. 61/666,719, filed Jun. 29, 2012, Boldog et al.
U.S. Appl. No. 61/666,733, filed Jun. 29, 2012, Nichols et al.
Annex 1—CTD Hunterase (6 pages).
Annex 1 (Proposed Amended Claims) Accompanying Patentee response to Notice of Opposition (Green Cross) to EA 034549 with English Translation dated Dec. 21, 2020 (4 pages).
Annex 2—Screenshot CTD Hunterase (5 pages).
Annex 3—Koshechkin & Rychikhin with English Abstract (4 pages).
Annex 4—USP39 with English Abstract (56 pages).

(Continued)

*Primary Examiner* — Christian L Fronda
(74) *Attorney, Agent, or Firm* — Proskauer Rose LLP

(57) ABSTRACT

The present invention provides, among other things, improved methods for purifying I2S protein produced recombinantly for enzyme replacement therapy. The present invention is, in part, based on the surprising discovery that recombinant I2S protein can be purified from unprocessed biological materials, such as, I2S-containing cell culture medium, using a process involving as few as four chromatography columns.

13 Claims, 12 Drawing Sheets

Specification includes a Sequence Listing.

(56) References Cited

U.S. PATENT DOCUMENTS

2024/0043817 A1 2/2024 Nichols

FOREIGN PATENT DOCUMENTS

| | | | |
|---|---|---|---|
| JP | 2002017376 A | 1/2002 |
| JP | 2006517412 A | 7/2006 |
| JP | 2011509674 A | 3/2011 |
| KR | 101158673 B1 | 7/2012 |
| WO | 8906279 A1 | 7/1989 |
| WO | 0050443 A2 | 8/2000 |
| WO | 0118022 A1 | 3/2001 |
| WO | 0155411 A2 | 8/2001 |
| WO | 0160991 A2 | 8/2001 |
| WO | 0170804 A1 | 9/2001 |
| WO | 0177137 A1 | 10/2001 |
| WO | 02059327 A2 | 8/2002 |
| WO | 02098455 A2 | 12/2002 |
| WO | 2004062592 A2 | 7/2004 |
| WO | 2004072275 A2 | 8/2004 |
| WO | 2005073367 A1 | 8/2005 |
| WO | 2005113765 A2 | 12/2005 |
| WO | 2009091994 A2 | 7/2009 |
| WO | 2011044542 A1 | 4/2011 |
| WO | 2011108451 A1 | 9/2011 |
| WO | 2011163649 A2 | 12/2011 |
| WO | 2011163652 A2 | 12/2011 |
| WO | 2012012718 A2 | 1/2012 |
| WO | 2012042857 A1 | 4/2012 |
| WO | 2012101671 A1 | 8/2012 |
| WO | 2012101998 A1 | 8/2012 |
| WO | 2012177020 A2 | 12/2012 |
| WO | 2014005014 A2 | 1/2014 |
| WO | 2014005019 A2 | 1/2014 |

OTHER PUBLICATIONS

Appeal Against the Decision Adopted on the Basis of the Results of Consideration of Opposition Against the Grant of EA Patent No. 034549, Green Cross Corporation, Apr. 28, 2022 (128 pages).
Article 216 of the Korean Patent Acts with English Translation, Jul. 1, 2011, (4 pages).
Article 44 of the Korean Utility Model Act with English Translation, Mar. 15, 2012 (4 pages).
Articles 41 and 87 of the Korean Patent Acts with English Translation, Mar. 15, 2012, (5 pages).
Brief of the patent holder on appeal against the decision of the EAPO made as a result of consideration of opposition against the grant of EA Patent No. 034549, Patentee Appeal Response Brief as filed Jul. 4, 2022 (13 pages).
Claim set accompanying letter responding to wish to proceed Communication on EP 2874649, dated Nov. 1, 2016 (2 pages).
Claim set of EP 2874649 B1 (2 pages).
Corrected Translation of Figures 16 and 17 for U.S. Appl. No. 61/500,994, (2 pages).
Institution Decision of Inter Partes Review in respect of U.S. Pat. No. 9,051,556, United States Patent and Trademark Office, entered May 25, 2016 (23 pages).
Final Written Decision of Inter Partes Review in respect of U.S. Pat. No. 9,051,556, United States Patent and Trademark Office, entered Mar. 22, 2017 (26 pages).
Inter Partes Review Certificate in respect of U.S. Pat. No. 9,051,556, United States Patent and Trademark Office, issued Jan. 5, 2021 (2 pages).
Decision of Opposition to EP 2867245 dated Mar. 10, 2021 (75 pages).
Decision on upholding Eurasian Patent as amended, EA Patent No. 034549 dated Dec. 28, 2021 (15 pages).
Decision on Appeal upholding Eurasian Patent as amended, EA Patent No. 034549 dated Feb. 14, 2023 (16 pages).
EMBL Nucleotide Sequence Database, Database Accession No. AAB88402, May 23, 2001 (2 pages).
EMBL Nucleotide Sequence Database, Database Accession No. AAY95971, Dec. 5, 2000 (2 pages).
EMBL Nucleotide Sequence Database, Database Accession No. ABB62912, Mar. 26, 2002 (1 page).
EMBL Nucleotide Sequence Database, Database Accession No. BD551115, Sep. 18, 2002 (1 page).
EMBL Nucleotide Sequence Database, Database Accession No. P95060, May 1, 1997 (1 page).
EMBL Nucleotide Sequence Database, Database Accession No. Q7V5N5, Oct. 1, 2003 (1 page).
EMBL Nucleotide Sequence Database, Database Accession No. Q88HK3, Jun. 1, 2003 (1 page).
EMBL Nucleotide Sequence Database, Database Accession No. Q8FTJ8, Mar. 1, 2003 (1 page).
EMBL Nucleotide Sequence Database, Database Accession No. Q92WL9, Dec. 1, 2001 (1 page).
EMBL Nucleotide Sequence Database, Database Accession No. Q93PA2, Dec. 1, 2001 (1 page).
EMBL Nucleotide Sequence Database, Database Accession No. Q98BQ8, Oct. 1, 2001 (1 page).
EMBL Nucleotide Sequence Database, Database Accession No. Q9A921, Jun. 1, 2001 (1 page).
EMBL Nucleotide Sequence Database, Database Accession No. Q9F3C7, Mar. 1, 2001 (1 page).
EMBL Sequence Version Archive, EMBL Nucleotide Sequence Database, Database Accession No. AAAB01008987, Jul. 24, 2002 (2 pages).
EMBL Sequence Version Archive, EMBL Nucleotide Sequence Database, Database Accession No. AK076022, Dec. 13, 2002 (1 page).
Gel Electrophoresis of Proteins: A Practical Approach, Hames (Ed.), Third Edition, 1998, Oxford University Press, pp. 1-52 (71 pages).
Glycan Analysis conducted for GC1111, (1 page).
HCP Analysis conducted for GC1111 with English Translation, (4 pages).
HGF Limited, EP Patent No. 2867245, Appeal No. T0528/21, Letter of the Opponent dated Oct. 18, 2022 (8 pages).
HGF Limited, EP Patent No. 2867245, Appeal No. T0528/21-3.304, Letter of the Opponent dated Jun. 2, 2022 (16 pages).
Hunterase Brochure Tax Invoice, (4 pages).
Hunterase Brochure with English Translation of non-English sections, (15 pages).
Hunterase Information from Korean Food and Drug Administration with English Translation, 2012, (11 pages).
Hunterase Patent List from Korean Food and Drug Administration with English Translation, (4 pages).
Hunterase TV news broadcast with English Translation, (2 pages).
International Search Report and Written Opinion for PCT/US2013/048561 dated Dec. 12, 2013 (17 pages).
International Search Report and Written Opinion for PCT/US2013/048571 dated Dec. 12, 2013 (10 pages).
International Search Report and Written Opinion for PCT/US2013/048601 dated Dec. 3, 2013 (10 pages).
KIPO Civil Petition dated Jul. 2, 2021 (11 pages).
KIPO Civil Petitions dated Oct. 5, 2022 (11 pages).
KIPO Notification of Result of Civil Petition dated Mar. 14, 2022, (12 pages).
Label for ELAPRASE (idursulfase), Jul. 18, 2006 (11 pages).
Letter responding to the wish to proceed Communication on EP 2874649, dated Nov. 1, 2016 (4 pages).
Main Request Accompanying Patentee Response to Opposition of EP 2867245 dated Nov. 7, 2019 (5 pages).
Notice of Decision of Information Disclosure with English Translation dated Jul. 20, 2020, Korean Intellectual Property Office, (8 pages).
Notice of Decision of Information Disclosure with English Translation dated Jun. 23, 2020, Korean Intellectual Property Office, (8 pages).
Notice of Opposition (Generium) to EA Patent No. 034549 with English Translation, dated Aug. 19, 2020 (42 pages).
Notice of Opposition (Green Cross) to EA Patent No. 034549 with English Translation, dated Aug. 20, 2020 (73 pages).
Notice of Opposition to a European Patent for EP 2723369 dated Jan. 12, 2017 (14 pages).

(56) References Cited

OTHER PUBLICATIONS

Notice of Opposition to a European Patent for EP 2867245 dated Jun. 12, 2019 (36 pages).
Opponent (Generium) Motion to Settle for EA 034549 with English Translation dated Jul. 7, 2021 (4 pages).
Opponent (Generium) reply to Patentee Reply for EA 034549 with English Translation dated Jul. 7, 2021 (19 pages).
Opponent (Generium) Reply to Patentee Response with English Translation for EA 034549 dated Apr. 22, 2021 (27 pages).
Opponent (Green Cross) Reply to Patentee Response for EA 034549 dated Feb. 2021 (24 pages).
Opponent (Green Cross) Supplemental Reply for EA 034549 with English Translation dated Jul. 12, 2021 (6 pages).
Opponent Response Regarding Opposition to EP 2867245 dated Aug. 19, 2020 (22 pages).
Opponent Response Regarding Opposition to EP 2867245 dated Nov. 27, 2020 (6 pages).
Opponent Statement of Ground of Appeal to Decision of Opposition to EP 2867245 dated Jul. 19, 2021 (24 pages).
Patent Court Section No. 3 Decision, Case No. 2009 Heo 4872, dated Nov. 27, 2009 with English Translation, Korean Intellectual Property Office, (23 pages).
Patentee Reply to Appeal, European Patent No. 2867245, Dec. 2, 2021 (46 pages).
Patentee Reply to Opponent (Generium) Reply for EA 034549 with English Translation dated Jun. 11, 2021 (57 pages).
Patentee Reply to Opponent (Green Cross) Reply for EA 034549 with English Translation dated Jul. 16, 2021 (27 pages).
Patentee Reply to Opponent, European Patent No. 2867245, Aug. 2, 2022 (11 pages).
Patentee Response Regarding Opposition to EP 2867245 dated Oct. 23, 2020 (2 pages).
Patentee Response to Notice of Opposition (Generium) to EA 034549 with English Translation dated Feb. 19, 2021 (37 pages).
Patentee Response to Notice of Opposition (Green Cross) to EA 034549 with English Translation dated Dec. 21, 2020 (80 pages).
Patentee Response to Opposition of EP 2867245 dated Nov. 7, 2019 (22 pages).
Patentee Response to Settlement Offer for EA 034549 with English Translation dated Jul. 19, 2021 (10 pages).
Patentee Supplementary Brief on the Opposition (Green Cross) of EA 034549 with EnglishTranslation dated Apr. 26, 2021 (3 pages).
Preliminary Opinion, Appeal of Opposition of EP 2867245 dated Sep. 10, 2023 (40 pages).
Principles and Techniques of Biochemistry and Molecular Biology, Wilson and Walker (Eds.), Seventh Edition, 2010, (661 pages).
Protein Purification—Handbook, Amersham Biosciences, 2001, (98 pages).
Protein Purification, Bonner (Ed.), 2007, Taylor & Francis Group, New York, NY, pp. 1-23 and pp. 137-160, (56 pages).
Response by the Opponent in Opposition to EP 2723369, dated Sep. 13, 2017 (5 pages).
Response in Examination of EP 2867245 dated Sep. 2, 2016 (8 pages).
Response of the Patentee for EP 2867245 dated Nov. 24, 2017 (11 pages).
Supreme Court Section No. 1 Decision, Case No. 2009 Da 72056, dated Dec. 24, 2009 with English Translation, Korean Intellectual Property Office, (9 pages).
Tosoh Bioscience, "SEC Size Exclusion Chromatography", Brochure Code No. B15L34A, 2015, (32 pages).
U.S. Appl. No. 61/500,994 with English Translation, filed Jun. 24, 2011 (136 pages).
WAVE Now part of GE Healthcare Bio-Sciences AB, "Cultivation of cells on Hillex microcarriers using WAVE Bioreactors Systems 2/10 and 20/50", Cell Culture, pp. 1-53, (53 pages).
"18—Downstream Processing", Filtration and Purification in the Biopharmaceutical Industry, Jornitz and Meltzer (Eds.), Second Edition, 2008, Informa Healthcare USA, Inc., New York, NY, pp. 459-493, (38 pages).

"21041—DMEM/F-12, no phenol red", Technical Resources, ThermoFisher Scientific, Catalog No. 21041025, 2015, retrieved from URL: www.thermofisher.com/us/en/home/technical-resources/mediainformation.57.html (3 pages).
"ABP 501—Biosimilar Candidate to Adalimumab", FDA Arthritis Advisory Committee, Jul. 12, 2016, (109 pages).
"ATS Statement: Guideline for the Six-Minute Walk Test", American Journal of Respiratory and Critical Care Medicine, vol. 166, No. 1, 2002, pp. 111-117, (7 pages).
"Chapter 1—Pharmaceutical Biotechnology: The Arrival of Recombinant Proteins", Therapeutic Peptides and Proteins, Banga (Ed.), Second Edition, 2006, Taylor & Francis Group, Boca Raton, FL, pp. 1-36, (47 pages).
"CPMP Position Statement on DNA and Host Cell Proteins (HCP) Impurities, Routine Testing Versus Validation Studies", The European Agency for the Evaluation of Medicinal Products, Jun. 10, 1997, (2 pages).
"Declaration of Chiwon Kim", signed Jun. 4, 2019 (54 pages).
"Declaration of Chul-Soo Cheong", signed Apr. 24, 2019 (3 pages).
"Declaration of Dave Nichols", signed Aug. 11, 2016 (32 pages).
"Declaration of Ik-Soo Jang", signed Jul. 12, 2021 (2 pages).
"Declaration of Jinwook Seo", signed Oct. 28, 2020 (7 pages).
"Declaration of Jongkook Lee", signed Jul. 16, 2021 (9 pages).
"Declaration of Uijun Ahn", signed Jul. 14, 2021 (6 pages).
"Elaprase™ (idursulfase): Solution for intravenous infusion", published on Oct. 15, 2007 on the FDA website and available online at URL: https://www.accessdata.fda.gov/drugsatfda_docs/label/2007/125151s032lbl.pdf.
"Encyclopedia of Separation Science", Wilson (Ed.), 2000, Academic Press, pp. 4547-4552, (8 pages).
"Endogenous", Merriam-Webster Online Dictionary, retrieved Aug. 4, 2010 from URL: https://www.merriam-webster.com/dictionary/endogenous, (1 page).
"Enzyme Technologies: Pluripotent Players in Discovering Therapeutic Agents", Yang et al. (Eds.), 2014, John Wiley & Sons, Inc., pp. 303-319, (24 pages).
"Examination Guidelines", Patent and Utility Model Examination Guidelines, Korean Intellectual Property Office, Mar. 2012, (11 pages).
"Exogenous", Merriam-Webster Online Dictionary, retrieved Dec. 18, 2009 from URL: https://www.merriam-webster.com/dictionary/exogenous, (2 pages).
"Exploring Proteins: A Student's Guide to Experimental Skills and Methods", Price and Nairn (Eds.), 2009, Oxford University Press, Chapter 5, Section 5.1 (5 pages).
"Green Cross Corporation R&D Workshop "Let's Make a Strong Pharmaceutical Company through Beneficial Cycles of R&D"", Herald Business Newspaper, published May 12, 2012 (5 pages).
"Green Cross Gains Market Approval with the World's 2nd Orphan Dug for Hunter Syndrome in South Korea", Biospace, Jan. 27, 2012, (3 pages).
"Guidance for Industry: Scientific Considerations in Demonstrating Biosimilarity to a Reference Product", U.S. Department of Health and Human Services, Food and Drug Administration, Feb. 2012, pp. 1-22 (25 pages).
"Handbook of Size Exclusion Chromatography and Related Techniques", Wu (Ed.), Second Edition, 2004, Marcel Dekker, Inc., pp. 1-24 (26 pages).
"Iduronate 2-sulfatase isoform a preproprotein [*Homo sapiens*]", NCBI Reference Sequence NP_000193.1, May 14, 2011, retrieved from URL: https://www.ncbi.nlm.nih.gov/protein/NP_000193.1, (3 pages).
"International Nonproprietary Names for Pharmaceutical Substances (Inn)", Who Drug Information, vol. 25, No. 4, 2011, pp. 413 and 423, (2 pages).
"Ion exchange columns and media Selection Guide", GE Healthcare, 2008, (8 pages).
"Klebsiella pneumoniae atsB and atsA genes", GenBank Accession No. AJ131525, Apr. 14, 1999, (4 pages).
"Mammalian Cell Cultures for Biologics Manufacturing", Zhou and Kantardjieff (ED.), Advances in Biochemical Engineering/Biotechnology, vol. 139, 2014, Springer-Verlag Berlin Heidelberg, DOI: 10.1007/978-3-642-54050-9 (262 pages).

(56) References Cited

OTHER PUBLICATIONS

"Methods in Enzymology: Guide to Protein Purification", Abelson (Ed.), 2nd Edition, 2009, Elsevier, pp. 9-19 and pp. 121-127, (73 pages).

"Patent Examination Guidelines", Korean Intellectual Property Office, Dec. 2017, (957 pages).

"Patent Examination Guidelines", Korean Intellectual Property Office, pp. 237-238, as corrected Jun. 16, 2020, (4 pages).

"Plasmid Vectors", retrieved May 9, 2011 from URL: http://www.mfa.od.ua/page275.htm (2 pages).

"Points to Consider in the Manufacture and Testing of Monoclonal Antibody Products for Human Use", U.S. Department of Health and Human Services, Food and Drug Administration, Center for Biologics Evaluation and Research, Docket No. 94D-02059, Feb. 28, 1997, (50 pages).

"Residual Host Cell Protein Measurement in Biopharmaceuticals", The United States Pharmacopeial Convention, 2016, pp. 1416-1436, (21 pages).

"Scientific Discussion", European Public Assessment Report, European Medicines Agency (EMA), Jan. 2007, retrieved Jan. 8, 2016 from URL: https://www.ema.europa.eu/docs/en_GB/document_library/EPAR_-_Scientific_Discussion/human/000700/WC500023005.pdf, (43 pages).

"Specifications: Test Procedures and Acceptance Criteria for Biotechnological/Biological Products Q6B", International Conference on Harmonisation of Technical Requirements for Registration of Pharmaceuticals for Human Use, Mar. 10, 1999, (20 pages).

"State system for ensuring the uniformity of measurements. Units (as amended)", Interstate Standard GOST 8.417-2002, approved by the Interstate for Standardization, Metrology and Certification, Protocol No. 22 dated Nov. 6, 2002, state standard of the Russian Federation since Sep. 1, 2003 (62 pages).

"The 13th Korea New Drug Award Ceremony: Commemorative Sourcebook", Korean Drug Research Association, with English Translation, dated Feb. 29, 2012 (46 pages).

Abdella, Peter M., et al., "A new cleavable reagent for cross-linking and reversible immobilization of proteins", Biochemical and Biophysical Research Communications, vol. 87, No. 3, Apr. 13, 1979, pp. 734-742, DOI: 10.1016/0006-291x(79)92020-5, (9 pages).

Agrawal, Vishal, et al., "Strategies for Rapid Production of Therapeutic Proteins in Mammalian Cells", BioProcess International, vol. 10, No. 4, Apr. 2012, (10 pages).

Al Sawaf, S., et al., "Neurological findings in Hunter disease: Pathology and possible therapeutic effects reviewed", Journal of Inherited Metabolic Disease, vol. 31, No. 4, Aug. 2008, pp. 473-480, (8 pages).

Allen, David, et al., "Validation of Peptide Mapping for Protein Identity and Genetic Stability. Biologics and Biotechnology Section, Pharmaceutical Research and Manufacturers of America", Biologicals, vol. 24, No. 3, Sep. 1996, pp. 255-275, (21 pages).

Benjdia, Alhosna, et al., "First evidences for a third sulfatase maturation system in prokaryotes from E. coli aslB and ydeM deletion mutants", FEBS Letters, vol. 581, No. 5, Mar. 6, 2007, pp. 1009-1014, DOI: 10.1016/j.febslet.2007.01.076, (6 pages).

Bielicki, J., et al., "Expression, purification and characterization of recombinant human N-acetylgalactosamine-6-sulphatase", Biochemical Journal, vol. 311, No. 1, Oct. 1995, pp. 333-339, DOI: 10.1042/bj3110333, (7 pages).

Bielicki, J., et al., "Human liver iduronate-2-sulphatase. Purification, characterization and catalytic properties", The Biochemical Journal, vol. 271, No. 1, Oct. 1990, pp. 75-86, DOI: 10.1042/bj2710075, (12 pages).

Bielicki, J, et al., "Recombinant human iduronate-2-sulphatase: correction of mucopolysaccharidosis-type II fibroblasts and characterization of the purified enzyme", Biochemical Journal, vol. 289, No. 1, Jan. 1993, pp. 241-246, DOI: 10.1042/bj2890241, (6 pages).

Boado, Ruben J., et al., "AGT-181: Expression in CHO cells and pharmacokinetics, safety, and plasma iduronidase enzyme activity in Rhesus monkeys", Journal of Biotechnology, vol. 144, No. 2, Oct. 26, 2009, pp. 135-141, (8 pages).

Boado, Ruben J., et al., "Genetic engineering of a lysosomal enzyme fusion protein for targeted delivery across the human blood-brain barrier", Biotechnology and Bioengineering, vol. 99, No. 2, 2008, pp. 475-484, (10 pages).

Bonham-Carter, John, et al., "A Brief History of Perfusion Biomanufacturing", BioProcess International, vol. 9, No. 9, Oct. 2011, (5 pages).

Bracewell, Daniel G., et al., "The future of host cell protein (HCP) identification during process development and manufacturing linked to a risk-based management for their control", Biotechnology and Bioengineering, vol. 112, No. 9, Sep. 2015, pp. 1727-1737, (11 pages).

Braun, Stephen E., et al., "Metabolic correction and cross-correction of mucopolysaccharidosis type II (Hunter syndrome) by retroviral-mediated gene transfer and expression of human iduronate-2-sulfatase", Proceedings of the National Academy of Sciences, vol. 90, Dec. 1993, pp. 11830-11834, (5 pages).

Burgess, Richard R., "Protein Purification", Proteomics of the Nervous System, 1st Ed., Edited by H.G. Nothwang and S.E. Pfeiffer, 2008, (18 pages).

Burrow, T Andrew, et al., "Review of the use of idursulfase in the treatment of mucopolysaccharidosis II", Biologics, vol. 2, No. 2, 2008, pp. 311-320, (10 pages).

Butler, Michael, et al., "Chapter 7: The glycosylation of proteins in cell culture", Animal Cell Culture and Technology, Second Edition, 2004, Garland Science/BIOS Scientific Publishers, (37 pages).

Carta, Giorgio, et al., "", Protein Chromatography: Process Development and Scale-Up, Wiley-VCH Verlag GmbH & Co. KGaA, 2010, pp. 1-55 and 309-346, (109 pages).

Champion, Kathleen, et al., "Defining Your Product Profile and Maintaining Control Over It, Part 2 Challenges of Monitoring Host Cell Protein Impurities", BioProcess International, Sep. 2005, (5 pages).

Chennamsetty, Naresh, et al., "Design of therapeutic proteins with enhanced stability", Proceedings of the National Academy Sciences, vol. 106, No. 29, 2009, pp. 11937-11942, (6 pages).

Chica, Roberto A, et al., "Semi-rational approaches to engineering enzyme activity: combining the benefits of directed evolution and rational design", Current Opinion in Biotechnology, vol. 16, No. 4, Aug. 2005, pp. 378-384, DOI: 10.1016/j.copbio.2005.06.004, (7 pages).

Cho, Sung Yoon, et al., "Impact of Enzyme Replacement Therapy on Linear Growth in Korean Patients with Mucopolysaccharidosis Type II (Hunter Syndrome)", Journal of Korean Medical Science, vol. 29, No. 2, Feb. 2014, pp. 254-260, DOI: 10.3346/jkms.2014.29.2.254, (7 pages).

Chung, Yo Kyung, et al., "A biochemical and physicochemical comparison of two recombinant enzymes used for enzyme replacement therapies of hunter syndrome", Glycoconjugate Journal, vol. 31, 2014, pp. 309-315, DOI: 10.1007/s10719-014-9523-0, (7 pages).

Clarke, Lorne A, "Idursulfase for the treatment of mucopolysaccharidosis II", Expert Opinion on Pharmacotherapy, vol. 9, No. 2, 2008, pp. 311-317, DOI: 10.1517/14656566.9.2.311, (8 pages).

Cosma, Maria Pia, et al., "The Multiple Sulfatase Deficiency Gene Encodes an Essential and Limiting Factor for the Activity of Sulfatases", Cell, vol. 113, No. 4, May 16, 2003, pp. 445-456, DOI: 10.1016/S0092-8674(03)00348-9, (12 pages).

Cummings, Larry J., "Chapter 24 Protein Chromatography on Hydroxyapatite Columns", Methods in Enzymology, vol. 463, 2009, pp. 387-404, DOI: 10.1016/S0076-6879(09)63024-X (18 pages).

Dalm, Marcella C.F., et al., "Effect of Feed and Bleed Rate on Hybridoma Cells in an Acoustic Perfusion Bioreactor: Metabolic Analysis", Biotechnology Progress, vol. 23, No. 3, 2007, pp. 560-569, DOI: 10.1021/bp060323k, (10 pages).

Dalm, Marcella C.F., et al., "Effect of feed and bleed rate on hybridoma cells in an acoustic perfusion bioreactor: Part I. Cell density, viability, and cell-cycle distribution", Biotechnology and Bioengineering, vol. 88, No. 5, Dec. 5, 2004, pp. 547-557, DOI: https://doi.org/10.1002/bit.20287, (11 pages).

Daniele, A, et al., "Uptake of recombinant iduronate-2-sulfatase into neuronal and glial cells in vitro", Biochimica et Biophysica Acta (BBA)—Molecular Basis of Disease, vol. 1588, No. 3, Dec. 12, 2002, pp. 203-209, (7 pages).

(56) References Cited

OTHER PUBLICATIONS

Di Natale, Paola, et al., "Iduronate sulfatase from human placenta", Biochimica et Biophysica Acta (BBA)—General Subjects, vol. 839, No. 3, May 8, 1985, pp. 258-261, DOI: 10.1016/0304-4165(85)90006-6, (4 pages).

Diaz Jacques, Carlos Eduardo, et al., "Hunter syndrome: Long-term idursulfase treatment does not protect patients against DNA oxidation and cytogenetic damage", Mutation Research/Genetic Toxicology and Environmental Mutagenesis, vol. 835, Nov. 2018, pp. 21-24, DOI: 10.1016/j.mrgentox.2018.08.013, (4 pages).

Dierks, Thomas, et al., "Conversion of cysteine to formylglycine: A protein modification in the endoplasmic reticulum", Proceedings of the National Academy of Sciences USA, vol. 94, No. 22, Oct. 1997, pp. 11963-11968, DOI: 10.1073/pnas.94.22.11963, (6 pages).

Dierks, Thomas, et al., "Multiple Sulfatase Deficiency is Caused by Mutations in the Gene Encoding the Human Cα-Formylglycine Generating Enzyme", Cell, vol. 113, No. 4, May 16, 2003, pp. 435-444, DOI: 10.1016/s0092-8674(03)00347-7, (10 pages).

Dierks, Thomas, et al., "Sequence determinants directing conversion of cysteine to formylglycine in eukaryotic sulfatases", The EMBO Journal, vol. 18, No. 8, 1999, pp. 2084-2091, DOI: 10.1093/emboj/18.8.2084, (8 pages).

Doneanu, Catalin E, et al., "Analysis of host-cell proteins in biotherapeutic proteins by comprehensive online two-dimensional liquid chromatography/mass spectrometry", mAbs, vol. 4, No. 2, 2012, pp. 24-44, (21 pages).

Dowd, Jason E., et al., "Optimization and control of perfusion cultures using a viable cell probe and cell specific perfusion rates", Cytotechnology, vol. 42, 2004, pp. 35-45, DOI: 10.1023/A:1026192228471, (11 pages).

Drummond, D. Allan, et al., "The evolutionary consequences of erroneous protein synthesis", Nature Reviews Genetics, vol. 10, 2009, pp. 715-724, Author Manuscript (20 pages).

Dumetz, André C., et al., "Patterns of protein-protein interactions in salt solutions and implications for protein crystallization", Protein Science, vol. 16, No. 9, Sep. 2007, pp. 1867-1877, (11 pages).

Eto, Y, et al., "Multiple sulfatase deficiency (Mucosulfatidosis): Impaired degradation of labeled sulfated compounds in cultured skin fibroblasts in vivo", European Journal of Pediatrics, vol. 135, No. 1, 1980, pp. 85-89, DOI: 10.1007/BF00445900, (5 pages).

Evans, William, "Removing Aggregates in Monoclonal Antibody Purification", Pharmaceutical Technology, vol. 39, No. 3, (4 pages).

Fang, Qinghua, et al., "Post-translational Formylglycine Modification of Bacterial Sulfatases by the Radical S-Adenosylmethionine Protein AtsB", Journal of Biological Chemistry, vol. 279, No. 15, Apr. 2004, pp. 14570-14578, DOI: 10.1074/jbc.M313855200, (9 pages).

Farid, Suzanne S, et al., "Continuous bioprocessing: The real thing this time?", mAbs, vol. 6, No. 6, 2014, pp. 1357-1361, DOI: 10.4161/mabs.36151, (5 pages).

Felice, Brian R., "Safety Evaluation of Chronic Intrathecal Administration of Idursulfase-IT in Cynomolgus Monkeys", Toxicologic Pathology, vol. 39, 2011, pp. 879-892, DOI: 10.1177/0192623311409595, (14 pages).

Ferrante, Paola, et al., "Molecular and biochemical characterisation of a novel sulphatase gene: Arylsulfatase G (Arsg)", European Journal of Human Genetics, vol. 10, No. 12, 2002, pp. 813-818, DOI: 10.1038/sj.ejhg.5200887, (14 pages).

Fey, Jens, et al., "Characterization of Posttranslational Formylglycine Formation by Luminal Components of the Endoplasmic Reticulum*", Journal of Biological Chemistry, vol. 276, No. 50, Dec. 2001, pp. 47021-47028, DOI: 10.1074/jbc.M108943200, (8 pages).

Follman, Deborah K., et al., "Factorial screening of antibody purification processes using three chromatography steps without protein A", Journal of Chromatography A, vol. 1023, No. 1-2, 2004, pp. 79-85, (7 pages).

Fraldi, Alessandro, et al., "SUMF1 enhances sulfatase activities in vivo in five sulfatase deficiencies", Biochemical Journal, vol. 403, No. 2, Apr. 2007, pp. 305-312, DOI: 10.1042/BJ20061783, (8 pages).

Frantantoni, Joseph C., et al., "Hurler and Hunter Syndromes: Mutual Correction of the Defect in Cultured Fibroblasts", Science, New Series, vol. 162, No. 3853, 1968, pp. 570-572, (2 pages).

Froissart, Roseline, et al., "Processing of iduronate 2-sulphatase in human fibroblasts", Biochemical Journal, vol. 309, No. 2, Jul. 1995, pp. 425-430, (6 pages).

Garfin, David, "Chapter 7—Gel electrophoresis of proteins", Essential Cell Biology, vol. 1, Davey and Lord (Eds.), 2003, pp. 197-268, (74 pages).

Geigert, John, "9.2.1 Primary Amino Acid Sequence Variants", The Challenge of CMC Regulatory Compliance for Biopharmaceuticals and other Biologics, Second Edition, 2013, Springer, (20 pages).

Ghaderi, Darius, "Production platforms for biotherapeutic glycoproteins. Occurrence, impact, and challenges of non-human sialylation", Biotechnology and Genetic Engineering Review, vol. 28, No. 1, 2012, pp. 147-176, DOI: 10.5661/bger-28-147, (29 pages).

Graham, Laurie, et al., "Risk Assessments and Control Strategies for Host Cell Proteins: FDA Expectations and Experiences", U.S. Food and Drug Administration, CMC Strategy Forum, Washington, DC, Jan. 26, 2015, (13 pages).

Graslund, Susanne, et al., "Protein production and purification", Nature Methods, vol. 5, No. 2, Feb. 2008, pp. 135-146, DOI: 10.1038/nmeth.f.202 (13 pages).

Guiochon, Georges, et al., "Separation science is the key to successful biopharmaceuticals", Journal of Chromatography A, vol. 1218, No. 49, Dec. 9, 2011, pp. 8836-8858 (23 pages).

Gutiérrez, Andres H., et al., "Of [hamsters] and men", Human Vaccines & Immunotherapeutics, vol. 8, No. 9, 2012, pp. 1172-1174, DOI: 10.4161/hv.22378, (3 pages).

Hesse, Friedemann, et al., "Comparison of a Production Process in a Membrane-Aerated Stirred Tank and up to 1000-L Airlift Bioreactors Using BHK-21 Cells and Chemically Defined Protein-Free Medium", Biotechnology Progress, vol. 19, No. 3, 2003, pp. 833-843, DOI: 10.1021/bp0257630, (11 pages).

Hoffman, Ken, "Letter to the Editor: A Rational Approach to Process-Specific Host-Cell Protein Detection", BioProcess International, Dec. 2010, pp. 8-10, (2 pages).

Hoffman, Kenneth, "Strategies for Host Cell Protein Analysis", BioPharm, vol. 13, No. 5, May 2000, pp. 38-45 (9 pages).

Hogwood, Catherine EM, et al., "Host cell protein dynamics in recombinant CHO cells", Bioengineered, vol. 4, No. 5, 2013, pp. 288-291, DOI: 10.4161/bioe.23382, (4 pages).

Hossler, Patrick, et al., "Optimal and consistent protein glycosylation in mammalian cell culture", Glycobiology, vol. 19, No. 9, Sep. 2009, pp. 936-949, DOI: 10.1093/glycob/cwp079, (14 pages).

Hovgaard, Lars, et al., "Protein Purification", Pharmaceutical Formulation Development of Peptides and Proteins, Frokjaer and Hovgaard (Eds.), 2000, CRC Press, pp. 29-40, (25 pages).

Javid, Babak, et al., "Mycobacterial mistranslation is necessary and sufficient for rifampicin phenotypic resistance", Proceedings of the National Academy of Sciences, vol. 111, No. 3, 2014, pp. 1132-1137, DOI: 10.1073/pnas.1317580111, (6 pages).

Jayapal, Karthik P., et al., "Recombinant Protein Therapeutics from CHO Cells—20 Years and Counting", CHO Consortium, SBE Special Section, 2007, pp. 40-47, (8 pages).

Juengst, Eric T, "What next for human gene therapy?", BMJ, vol. 326, 2003, pp. 1410-1411, DOI: 10.1136/bmj.326.7404.1410, (2 pages).

Kim, Jung-JA P et al., "Carbohydrate recognition by the mannose-6-phosphate receptors", Current Opinion in Structural Biology, vol. 19, No. 5, Oct. 2009, pp. 534-542, DOI: 10.1016/j.sbi.2009.09.002, (9 pages).

Knaust, Andreas, et al., "Residues Critical for Formylglycine Formation and/or Catalytic Activity of Arylsulfatase", Biochemistry, vol. 37, No. 40, 1998, pp. 13941-13946, DOI: 10.1021/bi9810205, (52 pages).

Konstantinov, Konstantin, et al., "The "Push-to-Low" Approach for Optimization of High-Density Perfusion Cultures of Animal Cells", Cell Culture Engineering, vol. 101, 2006, pp. 75-98, DOI: 10.1007/10_016, (24 pages).

Landgrebe, Jobst, et al., "The human SUMF1 gene, required for posttranslational sulfatase modification, defines a new gene family

(56) References Cited

OTHER PUBLICATIONS which is conserved from pro- to eukaryotes", Gene, vol. 316, 2003, pp. 47-56, DOI: 10.1016/s0378-1119(03)00746-7, (10 pages).

Latypov, Ramil F., et al., "Elucidation of Acid-induced Unfolding and Aggregation of Human Immunoglobulin IgG1 and IgG2 Fc", Journal of Biological Chemistry, vol. 287, No. 2, 2012, pp. 1381-1396, (32 pages).

Lodish, Harvey, et al., "Chapter 3—Protein Structure and Function", Molecular Cell Biology, 7th Edition, 2000, pp. 59-113, (60 pages).

Madsen, James A, et al., "Toward the complete characterization of host cell proteins in biotherapeutics via affinity depletions, LC-MS/MS, and multivariate analysis", mAbs, vol. 7, No. 6, 2015, pp. 1128-1137, DOI: 10.1080/19420862.2015.1082017, (11 pages).

McDonald, Claudia A., et al., "Combining Results from Lectin Affinity Chromatography and Glycocapture Approaches Substantially Improves the Coverage of the Glycoproteome", Molecular & Cellular Proteomics, vol. 8, No. 2, Feb. 2009, pp. 287-301, DOI: 10.1074/mcp.M800272-MCP200, (15 pages).

Morimoto-Tomita, Megumi, et al., "Cloning and Characterization of Two Extracellular Heparin-degrading Endosulfatases in Mice and Humans*", Journal of Biological Chemistry, vol. 277, No. 51, Dec. 2002, pp. 49175-49185, DOI: 10.1074/jbc.M205131200, (11 pages).

Muenzer, Joseph, et al., "A phase I/II clinical trial of enzyme replacement therapy in mucopolysaccharidosis II (Hunter syndrome)", Molecular Genetics and Metabolism, vol. 90, No. 3, Mar. 2007, pp. 329-337, (10 pages).

Muenzer, Joseph, et al., "A phase II/III clinical study of enzyme replacement therapy with idursulfase in mucopolysaccharidosis II (Hunter syndrome)", Genetics in Medicine, vol. 8, No. 8, Aug. 2006, pp. 465-473, DOI: 10.1097/01.gim.0000232477.37660.fb, (9 pages).

Neufeld, Elizabeth F., "Chapter 10: Enzyme replacement therapy—a brief history", Fabry Disease: Perspective from 5 Years of FOS, Mehta, Beck, Sunder-Plassmann (Eds.), 2006, Oxford PharmaGenesis, Retrieved from URL: http://www.ncbi.nlm.nih.gov/books/NBK11588/?report=printable, (8 pages).

Parini, Rossella et al., "Intravenous Enzyme Replacement Therapy in Mucopolysaccharidoses: Clinical Effectiveness and Limitations", International Journal of Molecular Sciences, vol. 21, No. 8, 2020, (30 pages).

Popovic, M.K., et al., "Bioreactors and Cultivation Systems for Cell and Tissue Culture", Encyclopedia of Life Support Systems (EOLSS), 2012, (29 pages).

Rathore, Anurag S., et al., "Aggregation of Monoclonal Antibody Products: Formation and Removal", BioPharm International, vol. 26, No. 3, 2013, (5 pages).

Richter, Andreas, et al., "Novel Assay for Protein Impurities in Biopharmaceuticals Based on Fluorescence Intensity Distribution Analysis (FIDA)", Animal Cell Technology: From Target to Market, 2001, pp. 488-490, (5 pages).

Rivera-Colon, Yadilette, et al., "The Structure of Human GALNS Reveals the Molecular Basis for Mucopolysaccharidosis IV A", Journal of Molecular Biology, vol. 423, No. 5, Nov. 9, 2012, pp. 736-751, DOI: 10.1016/j.jmb.2012.08.020, (16 pages).

Rommerskirch, W, et al., "Multiple sulfatase deficiency: catalytically inactive sulfatases are expressed from retrovirally introduced sulfatase cDNAs", The Proceedings of the National Academy of Sciences USA, vol. 89, No. 7, 1992, pp. 2561-2565, DOI: 10.1073/pnas.89.7.2561, (5 pages).

Sang, Helen, "Prospects for transgenesis in the chick", Mechanisms of Development, vol. 121, No. 9, Sep. 2004, pp. 1179-1186, DOI: 10.1016/j.mod.2004.05.012, (8 pages).

Schirmer, Andreas, et al., "Computational analysis of bacterial sulfatases and their modifying enzymes", Chemistry & Biology, vol. 5, No. 8, 1998, pp. 181-186, DOI: 10.1016/s1074-5521(98)90154-5, (6 pages).

Schmidt, Bernhard, et al., "A novel amino acid modification in sulfatases that is defective in multiple sulfatase deficiency", Cell, vol. 82, 1995, pp. 271-278, DOI: 10.1016/0092-8674(95)90314-3, (2 pages).

Scopes, Robert K., "Chapter 12: Optimization of Procedures; Final Steps", Protein Purification: Principles and Practices, Third Edition, 2010, Springer Science+Business Media, Inc., pp. 310-345, (51 pages).

Sen, S., et al., "Developments in Directed Evolution for Improving Enzyme Functions", Applied Biochemistry and Biotechnology, vol. 143, 2007, pp. 212-223, DOI: 10.1007/s12010-007-8003-4, (12 pages).

Shukla, Abhinav A., et al., "Chapter 6—Modes of Preparative Chromatography", Process Scale Bioseparations for the Biopharmaceutical Industry, 2007, pp. 179-225 (62 pages).

Singh, Raushan Kumar, et al., "Protein Engineering Approaches in the Post-Genomic Era", Current Protein and Peptide Science, vol. 18, 2017, pp. 1-11, (11 pages).

Skoog, Douglas A., et al., Principles of Instrumental Analysis, 6th Edition, 2007, Brooks/Cole, Cengage Learning, pp. 816-855, (43 pages).

Slade, Susam, et al., "Chapter 6: Protein purification", Essential Cell Biology, vol. 1, No. 262, Davey and Lord (Eds.), 2003, pp. 163-195, (35 pages).

Sleat, David E., et al., "Identification of Sites of Mannose 6-Phosphorylation on Lysosomal Proteins", Molecular & Cellular Proteomics, vol. 5, No. 4, 2006, pp. 686-701, DOI: 10.1074/mcp.M500343-MCP200, (16 pages).

Sohn, Young Bae, et al., "Phase I/II clinical trial of enzyme replacement therapy with idursulfase beta in patients with mucopolysaccharidosis II (Hunter Syndrome)", Orphanet Journal of Rare Diseases, vol. 8, Article No. 42, 2013, DOI: 10.1186/1750-1172-8-42, (17 pages).

Sohn, Young Bae, et al., "Safety and efficacy of enzyme replacement therapy with idursulfase beta in children aged younger than 6 years with Hunter syndrome", Molecular Genetics and Metabolism, vol. 114, No. 2, Feb. 2015, pp. 156-160, DOI: 10.1016/j.ymgme.2014.08.009.

Sukegawa-Hayasaka, K., et al., "Effect of Hunter disease (mucopolysaccharidosis type II) mutations on molecular phenotypes of iduronate-2-sulfatase: Enzymatic activity, protein processing and structural analysis", Journal of Inherited Metabolic Disease, vol. 29, No. 6, Dec. 2006, pp. 755-761, (7 pages).

Swiech, Kamilla, et al., "Human cells: New platform for recombinant therapeutic protein production", Protein Expression and Purification, vol. 84, No. 1, Jul. 2012, pp. 147-153, DOI: 10.1016/j.pep.2012.04.023, (8 pages).

Szameit, Claudia, et al., "The Iron Sulfur Protein AtsB is Required for Posttranslational Formation of Formylglycine in the Klebsiella Sulfatase*", The Journal of Biological Chemistry, vol. 274, No. 22, May 1999, pp. 15375-15381, (7 pages).

Tomatsu, Shunji, et al., "Morquio disease: Isolation, characterization and expression of full-length cDNA for human N-acetylgalactosamine-6-sulfate sulfatase", Biochemical and Biophysical Research Communications, vol. 181, No. 2, Dec. 16, 1991, pp. 677-683, DOI: 10.1016/0006-291x(91)91244-7, (7 pages).

Tong, Patrick Y., et al., "Ligand interactions of the cation-dependent mannose 6-phosphate receptor", The Journal of Biological Chemistry, vol. 264, No. 14, 1989, pp. 7970-7975, (6 pages).

Uribe, Alfredo, et al., "Selective Screening for Lysosomal Storage Diseases with Dried Blood Spots Collected on Filter Paper in 4,700 High-Risk Colombian Subjects", JIMD Reports, vol. 11, 2013, pp. 107-116, DOI: 10.1007/8904_2013_229, (10 pages).

Valente, Kristin N., et al., "Expression of difficult-to-remove host cell protein impurities during extended Chinese hamster ovary cell culture and their impact on continuous bioprocessing", Biotechnology and Bioengineering, vol. 112, No. 6, 2015, pp. 1232-1242, DOI: 10.1002/bit.25515, (11 pages).

Voisard, D., et al., "Potential of cell retention techniques for large-scale high-density perfusion culture of suspended mammalian cells", Biotechnology and Bioengineering, vol. 82, No. 7, Jun. 30, 2003, pp. 751-765, DOI: 10.1002/bit.10629, (15 pages).

(56) References Cited

OTHER PUBLICATIONS

Voznyi, Ya. V., et al., "A fluorimetric enzyme assay for the diagnosis of MPS II (Hunter disease)", Journal of Inherited Hetabolic Disease, vol. 24, No. 6, Nov. 2001, pp. 675-680, (6 pages).

Wang, Fengqiang, et al., "Host-Cell Protein Measurement and Control", BioPharm International, vol. 28, No. 6, Jun. 2015, pp. 32-38, (7 pages).

Wang, Xing, et al., "Host cell proteins in biologics development: Identification, quantitation and risk assessment", Biotechnology and Bioengineering, vol. 103, No. 3, 2009, pp. 446-458, DOI: 10.1002/bit.22304, (13 pages).

Wang, Xing, et al., "Improved HCP Quantitation by Minimizing Antibody Cross-Reactivity to Target Proteins", BioProcess International, 2010, pp. 18-24, (5 pages).

Wasteson, Ake, et al., "[51] Iduronate sulfatase from human plasma", Methods in Enzymology, vol. 83, 1982, pp. 573-578, DOI: 10.1016/0076-6879(82)83053-x, (6 pages).

Whitley, Chester B., et al., "Diagnostic test for mucopolysaccharidosis. II. Rapid quantification of glycosaminoglycan in urine samples collected on a paper matrix", Clinical Chemistry, vol. 35, No. 10, 1989, pp. 2074-2081, (8 pages).

Wilson, P. J., et al., "Hunter syndrome: isolation of an iduronate-2-sulfatase cDNA clone and analysis of patient DNA.", The Proceedings of the National Academy of Sciences, vol. 87, No. 21, 1990, (5 pages).

Wolter, Tanja, et al., "Assays for Controlling Host-Cell Impurities in Biopharmaceuticals", BioProcess International, Feb. 2005, (5 pages).

Wraith, James E., et al., "The clinical phenotype of two patients with a complete deletion of the iduronate-2-sulphatase gene (mucopolysaccharidosis II—Hunter syndrome)", Human Genetics, vol. 87, 1991, pp. 205-206, DOI: 10.1007/BF00204183, (2 pages).

Written Decision, Appeal of Opposition of EP 2867245 dated Nov. 22, 2023 (39 pages).

Yang, Yi, et al., "Detecting low level sequence variants in recombinant monoclonal antibodies", mAbs, vol. 2, No. 3, 2010, pp. 285-298, DOI: 10.4161/mabs.2.3.11718, (14 pages).

Yavorsky, David, et al., "The Clarification of Bioreactor Cell Cultures for Biopharmaceuticals", Pharmaceutical Technology, vol. 27, No. 3, 2003, pp. 62-76, (8 pages).

Yutaka, Tohru, et al., "Purification and Some Properties of Human Liver Iduronate Sulfatase", The Journal of Biochemistry, vol. 91, No. 2, 1982, pp. 433-442, DOI: 10.1093/oxfordjournals.jbchem.a133715, (9 pages).

Zenk, Anne, et al., "Low Level Sequence Variant Analysis of Recombinant Proteins: An Optimized Approach", PLoS One, vol. 7, No. 7, 2012, e40328, DOI: 10.1371/journal.pone.0040328, (10 pages).

Zhou, Qing-Hui, "Brain-Penetrating IgG-Iduronate 2-Sulfatase Fusion Protein for the Mouse", Drug Metabolism and Disposition, vol. 40, No. 2, 2012, pp. 329-335, (8 pages).

* cited by examiner

| LANE | LOAD SAMPLE | LOAD VOLUME | TOTAL µg |
|---|---|---|---|
| 1 | PROTEIN STDS | 3 µl | |
| 2 | ASSAY CONTROL #1 | 20 µl | 8 µg |
| 3 | ASSAY CONTROL #2 | 20 µl | 16 µg |
| 4 | I2S REFERENCE STANDARD | 20 µl | 8 µg |
| 5 | I2S-AF 2D SERUM-FREE CULTURE | 20 µl | 8 µg |
| 6 | I2S-AF 4D SERUM-FREE CULTURE | 20 µl | 8 µg |

METHODS AND COMPOSITIONS FOR TREATMENT OF HUNTER SYNDROME COMPRISING IDURONATE-2-SULFATASE

This application is a continuation application of U.S. application Ser. No. 18/052,442, filed on Nov. 3, 2022, which is a continuation application of U.S. application Ser. No. 17/092,034, filed on Nov. 6, 2020, now U.S. Pat. No. 11,530,393, which is a continuation application of U.S. application Ser. No. 16/417,440, filed on May 20, 2019, now abandoned, which is a divisional application of U.S. application Ser. No. 15/279,018, filed on Sep. 28, 2016, now U.S. Pat. No. 10,344,270, which is a divisional application of U.S. application Ser. No. 14/673,607, filed on Mar. 30, 2015, now U.S. Pat. No. 9,492,511, which is a divisional application of U.S. application Ser. No. 13/829,706, filed on Mar. 14, 2013, now U.S. Pat. No. 9,051,556, which claims benefit of U.S. Provisional Patent Application No. 61/666,733, filed Jun. 29, 2012, each of which are hereby incorporated by reference in their entireties.

SEQUENCE LISTING

The present specification makes reference to a Sequence Listing submitted in electronic form as an ST.26.xml file named "SHR-1087US6_20221031_SL" on Oct. 31, 2022. The.xml file was generated on Oct. 31, 2022, and is 7 Kilobytes in size. The entire contents of the Sequence Listing are herein incorporated by reference.

BACKGROUND

Mucopolysaccharidosis type II (MPS II, Hunter syndrome) is an X-chromosome-linked recessive lysosomal storage disorder that results from a deficiency in the enzyme iduronate-2-sulfatase (I2S). I2S cleaves the terminal 2-O-sulfate moieties from the glycosaminoglycans (GAG) dermatan sulfate and heparan sulfate. Due to the missing or defective I2S enzyme in patients with Hunter syndrome, GAG progressively accumulate in the lysosomes of a variety of cell types, leading to cellular engorgement, organomegaly, tissue destruction, and organ system dysfunction.

Generally, physical manifestations for people with Hunter syndrome include both somatic and neuronal symptoms. For example, in some cases of Hunter syndrome, central nervous system involvement leads to developmental delays and nervous system problems. While the non-neuronal symptoms of Hunter Syndrome are generally absent at birth, over time the progressive accumulation of GAG in the cells of the body can have a dramatic impact on the peripheral tissues of the body. GAG accumulation in the peripheral tissue leads to a distinctive coarseness in the facial features of a patient and is responsible for the prominent forehead, flattened bridge and enlarged tongue, the defining hallmarks of a Hunter patient. Similarly, the accumulation of GAG can adversely affect the organ systems of the body. Manifesting initially as a thickening of the wall of the heart, lungs and airways, and abnormal enlargement of the liver, spleen and kidneys, these profound changes can ultimately lead to widespread catastrophic organ failure. As a result, Hunter syndrome is always severe, progressive, and life-limiting.

Enzyme replacement therapy (ERT) is an approved therapy for treating Hunter syndrome (MPS II), which involves administering exogenous replacement I2S enzyme to patients with Hunter syndrome.

SUMMARY OF THE INVENTION

The present invention provides, among other things, improved methods for purifying I2S protein produced recombinantly for enzyme replacement therapy. The present invention is, in part, based on the surprising discovery that recombinant I2S protein can be purified from unprocessed biological materials, such as, I2S-containing cell culture medium, using a process involving as few as four chromatography columns. Approved existing purification process of recombinant I2S for enzyme replacement therapy involves 6 chromatography columns. As described in the Examples section, recombinant I2S proteins purified using a four-column process according to the invention conforms with the marketing purity requirements in the US and many other countries. In addition, the recombinant I2S enzyme purified according to the present invention retains high percentage of Ca-formylglycine (FGly) (e.g., higher than 70% and up to 100%), which is important for the activity of I2S enzyme, and distinct characteristics such as sialic acid content and glycan map that may facilitate bioavailability and/or lysosomal targeting of the recombinant I2S protein. Therefore, the present invention provides an effective, cheaper, and faster process for purifying recombinant I2S protein. The present invention is particularly useful for purifying recombinant I2S protein produced in serum-free medium.

Thus, in one aspect, the present invention provides a method of purifying recombinant I2S protein from an impure preparation using a process based on one or more of anion-exchange chromatography, cation-exchange chromatography, mixed-mode chromatography, and hydrophobic interaction chromatography. In some embodiments, an inventive method according to the present invention involves less than 6 (e.g., less than 5, less than 4, or less than 3) chromatography steps. In some embodiments, an inventive method according to the present invention involves 2, 3, 4 or 5 chromatography steps. In some embodiments, an inventive method according to the present invention involves 4 chromatography steps. In some embodiments, the purified recombinant I2S protein according to the present invention contains less than 100 ng/mg Host Cell Protein (HCP) (e.g., less than 90 ng/mg HCP, less than 80 ng/mg HCP, less than 70 ng/mg HCP, less than 60 ng/mg HCP, less than 50 ng/mg HCP, less than 40 ng/mg HCP, less than 30 ng/mg HCP, less than 20 ng/mg HCP, less than 10 ng/mg HCP).

In some embodiments, a suitable anion-exchange chromatography is Q chromatography. In some embodiments, a suitable cation-exchange chromatography is SP chromatography. In some embodiments, a suitable mixed-mode chromatography is hydroxyapatite (HA) chromatography. In some embodiments, a suitable hydrophobic interaction chromatography is phenyl chromatography.

It is contemplated that anion-exchange chromatography (e.g., O column), cation-exchange chromatography (e.g., SP column), mixed-mode chromatography (e.g., HA column), and hydrophobic interaction chromatography (e.g., phenyl column) can be carried out in any order. In some embodiments, a method according to the present invention carries out anion-exchange chromatography (e.g., O column), cation-exchange chromatography (e.g., SP column), mixed-mode chromatography (e.g., HA column), and hydrophobic interaction chromatography (e.g., phenyl column) in that order.

In some embodiments, an impure preparation or an intermediate eluate or flow-through is adjusted to pH of about 5.0-7.0 (e.g., about 5.0, 5.5, 6.0, 6.5 or 7.0) and the conductivity of about 10-20 mS/cm (e.g., 10, 11, 12, 13, 14, 15, 16, 17, 18, 19, or 20 mS/cm) prior to loading to the anion-exchange chromatography column (e.g., Q column). In some embodiments, the pH is adjusted using IM sodium acetate. In some embodiments, the conductivity is adjusted using 5 M sodium chloride. In some embodiments, the anion-exchange chromatography column, once loaded, is washed using a wash buffer comprising salt (e.g., NaCl) concentration ranging from about 140 mM to 200 mM (e.g., about 140 mM, 145 mM, 150 mM, 155 mM, 160 mM, 165 mM, 170 mM, 175 mM, 180 mM, 185 mM, 190 mM, 195 mM, or 200 mM) with pH of about 5.0-7.0 (e.g., about 5.0, 5.5, 6.0, 6.5 or 7.0). In some embodiments, the anion-exchange chromatography column is eluted using a elution buffer comprising a linear salt (e.g., NaCl) gradient. In some embodiments, a suitable linear NaCl gradient contains a range from about 0-500 mM NaCl (e.g., about 0-400 mM, about 0-350 mM, about 0-300 mM, about 50-500 mM, about 150-500 mM, about 150-450 mM, about 150-400 mM).

In some embodiments, an impure preparation or an intermediate eluate or flow-through is adjusted to conductivity ranging between about 1 mS/cm and 20 mS/cm (e.g., between about 1 mS/cm and 15 mS/cm, between about 1 mS/cm and 10 mS/cm, between about 1 mS/cm and 8 mS/cm, between about 1 mS/cm and 6 mS/cm, between about 1 mS/cm and 4 mS/cm, between about 2 mS/cm and 4 mS/cm) prior to loading to the cation-exchange chromatography column (e.g., SP column). In some embodiments, an impure preparation or an intermediate cluate or flow-through is adjusted to conductivity ranging between n about 2 mS/cm and 4 mS/cm (e.g., 2, 2.5, 3, 3.5, or 4 mS/cm) prior to loading to the cation-exchange chromatography column (e.g., SP column). In some embodiments, the conductivity is adjusted by diluting the cluate from the anion-exchange chromatography column with $H_2O$ at about 1-2:1 (e.g., 1:1, 1.1:1, 1.2:1, 1.3:1, 1.4:1.5:1, 1.6:1, 1.7:1, 1.8:1, 1.9:1, or 2:1) ratio. In some embodiments, the conductivity is adjusted by dialfiltration. In some embodiments, the cation-exchange chromatography column is run at a pH of about 5.0-6.5 (e.g., about 5.0, 5.5, 6.0 or 6.5). In some embodiments, the cation-exchange chromatography column is run with a buffer comprising phosphate (e.g., NaPO4) concentration ranging from about 0.01 M to about 0.1 M (e.g., about 0.01 M, 0.02 M, 0.03 M, 0.04 M, 0.05 M, 0.06 M, 0.07 M, 0.08 M, 0.09 M, or 0.1 M). In some embodiments, a suitable pH is about 5.0-6.5 (e.g., about 5.0, 5.5, 6.0, or 6.5).

In some embodiments, an impure preparation or an intermediate eluate or flow-through is adjusted to phosphate (e.g., NaPO4) concentration ranging from about 0.001 M to about 0.01 M (e.g., about 0.001 M, 0.002 M, 0.003 M, 0.004 M, 0.005 M, 0.006 M, 0.007 M, 0.008 M, 0.009 M, or 0.01 M) and pH of about 5.0-6.5 (e.g., about 5.0, 5.5, 6.0, or 6.5) prior to loading the mixed-mode chromatography column (e.g., HA column). In some embodiments, the mixed-mode chromatography column (e.g., HA column), once loaded, is washed with a wash buffer containing phosphate (e.g., 1-10 mM sodium or potassium phosphate) at or near neutral pH. In some embodiments, the loaded mixed-mode chromatography column (e.g., HA column) is washed with a wash buffer having a phosphate concentration ranging from about 10-20 mM (e.g., about 10-18 mM, 10-16 mM, 10-15 mM, 12-20 mM, 14-18 mM, 14-16 mM). In some embodiments, the loaded mixed-mode chromatography column (e.g., HA column) is washed with a wash buffer having a phosphate concentration of or greater than 10 mM, 11 mM, 12 mM, 13 mM, 14 mM, 15 mM, 16 mM, 17 mM, 18 mM, 19 mM, 20 mM. In some embodiments, elution from a mixed-mode chromatography column (e.g., HA column) is achieved with a gradient phosphate buffer. In some embodiments, a suitable elution buffer may have a phosphate gradient of approximately 1-400 mM (e.g., 1-300 mM, 1-200 mM, 1-150 mM, 1-100 mM, 10-350 mM, 10-300 mM, 10-250 mM, 10-200 mM, 10-150 mM, 10-140 mM, 10-130 mM, 10-120 mM, 10-110 mM, 10-100 mM, 10-90 mM, 10-80 mM, 10-70 mM, 10-60 mM, 10-50 mM) sodium phosphate or potassium phosphate. In some embodiments, elution from an HA column is achieved by stepwise increasing the phosphate concentration in the elution buffer. In some embodiments, stepwise elution buffers may have a phosphate (e.g., sodium phosphate) concentration selected from 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 200 mM, 250 mM, 300 mM, 350 mM, 400 mM. In some embodiments, elution from a mixed-mode chromatography column (e.g., HA column) is achieved by an elution buffer having a phosphate (e.g., sodium phosphate) concentration ranging from about 50 mM to 150 mM (e.g., selected from the phosphate (e.g., sodium phosphate) concentration of 50 mM, 60 mM, 70 mM, 80 mM, 90 mM, 100 mM, 110 mM, 120 mM, 130 mM, 140 mM, 150 mM, and combination thereof).

In some embodiments, an impure preparation or an intermediate eluate or flow-through is adjusted to salt (e.g., NaCl) concentration ranging from about 0.5 M to about 2.0 M (e.g., about 0.5 M, 1.0 M, 1.1 M, 1.2 M, 1.3 M, 1.4 M, 1.5 M, 1.6 M, 1.7 M, 1.8 M, 1.9 M, or 2.0 M NaCl) at pH of about 4.5-6.0 (e.g., about 4.5, 5.0, 5.5, or 6.0) prior to loading onto the hydrophobic interaction chromatography column (e.g., phenyl column). In some embodiments, the hydrophobic interaction chromatography column, once loaded, is washed using a wash buffer comprising salt (e.g., NaCl) concentration ranging from about 0.5 M to 2.0 M (e.g., about 0.5 M, 1.0 M, 1.1 M, 1.2 M, 1.3 M, 1.4 M, 1.5 M, 1.6 M, 1.7 M, 1.8 M, 1.9 M, or 2.0 M NaCl) at pH of about 4.5-6.0 (e.g., about 4.5, 5.0, 5.5, or 6.0). In some embodiments, the hydrophobic interaction chromatography column is eluted using a elution buffer comprising salt (e.g., NaCl) concentration ranging from about 0.1 M to about 0.5 M (e.g., about 0.1 M, 0.2 M, 0.3 M, 0.4 M, or 0.5 M NaCl) at pH of about 4.5-6.0 (e.g., about 4.5, 5.0, 5.5, or 6.0).

In some embodiments, each of the anion-exchange chromatography, cation-exchange chromatography, mixed-mode chromatography, and hydrophobic interaction chromatography column has a height ranging from 14-25 cm (e.g., 15-25 cm, 15-20 cm, 14-24 cm, 14-22 cm, 14-20 cm, or 16-18 cm). In some embodiments, each of the anion-exchange chromatography, cation-exchange chromatography, mixed-mode chromatography, and hydrophobic interaction chromatography column has a height of approximately 14, 15, 16, 17, 18, 19, 20, 21, 22, 23, 24, or 25 cm.

In some embodiments, an inventive method according to the present invention includes a step of viral inactivation before loading the impure preparation onto the first chromatography column. In some embodiments, the step of viral inactivation includes adding a detergent to the impure preparation. In some embodiments, an inventive method according to the invention further includes a step of viral removal after the last Chromatography column. In some embodiments, a method of the invention further includes a step of ultrafiltration and/or dialfiltration. In some embodiments, the step of ultrafiltration and/or dialfiltration includes exchanging the purified recombinant 12S protein into a drug formulation buffer.

In some embodiments, the present invention is used to purify a recombinant 12S protein having an amino acid sequence at least about 50% (e.g., at least about 55%, 60%, 65%, 70%, 75%, 80%, 85%, 90%, 95%, 96%, 97%, 98%, 99%) identical to SEQ ID NO:1. In some embodiments, the present invention is used to purify a recombinant I2S protein having an amino acid sequence identical to SEQ ID NO:1.

In some embodiments, the present invention is used to purify a recombinant I2S protein produced by mammalian cells cultured in suspension in a serum-free medium. In some embodiments, a serum-free medium suitable for the invention lacks animal-derived components. In some embodiments, a serum-free medium suitable for the invention is a chemically-defined medium. In some embodiments, the mammalian cells are cultured in a bioreactor. In some embodiments, the mammalian cells co-express the recombinant I2S protein and formylglycine generating enzyme (FGE). In some embodiments, the mammalian cells are human cells.

In some embodiments, an impure preparation used in a method of the invention is prepared from the serum-free medium containing recombinant I2S protein secreted from the mammalian cells. In some embodiments, an impure preparation used in a method of the invention is thawed from a frozen medium preparation.

In some embodiments, a purified recombinant I2S protein according to the present invention contains, on average, 16-22 (e.g., 16-21, 16-20, 16-19, 17-22, 17-21, 17-20, 17-19) sialic acids per molecule. In some embodiments, a purified recombinant I2S protein according to the present invention contains, on average, 16, 17, 18, 19, 20, 21, or 22 sialic acids per molecule.

In some embodiments, a purified recombinant I2S protein according to the present invention has at least about 70% (e.g., at least about 77%, 80%, 85%, 90%, 95%, 96%, 97%, 98%, 99%) conversion of the cysteine residue corresponding to Cys59 of human I2S (SEQ ID NO: 1) to Ca-formylglycine (FGly). In some embodiments, a purified recombinant I2S protein according to the present invention has substantially 100% conversion of the cysteine residue corresponding to Cys59 of human I2S (SEQ ID NO:1) to Ca-formylglycine (FGly). In some embodiments, a purified recombinant I2S protein according to the present invention has specific activity of at least 20 U/mg, 30 U/mg, 40 U/mg. 50 U/mg. 60 U/mg. 70 U/mg. 80 U/mg. 90 U/mg. or 100 U/mg as determined by an in vitro sulfate release activity assay using heparin disaccharide as substrate.

In some embodiments, a purified recombinant I2S protein according to the present invention is characterized with cellular uptake of greater than 70%, 75%, 80%, 85%, 90%, 95%, as determined by an in vitro uptake assay.

In some embodiments, a purified recombinant I2S protein according to the present invention is characterized with a glycan map comprising seven peak groups indicative of neutral (peak group 1), mono-sialylated (peak group 2), di-sialylated (peak group 3), monophosphorylated (peak group 4), tri-sialylated (peak group 5), tetra-sialylated (peak group 6), and diphosphorylated (peak group 7) I2S protein, respectively. In some embodiments, the glycan map is generated following a neuraminidase digestion. In other embodiments, the glycan map is generated following an alkaline phosphatase digestion.

Among other things, the present invention provides purified recombinant I2S protein as described herein, and pharmaceutical compositions or formulation containing the same. In some embodiments, a formulation is formulated for intravenous, subcutaneous and/or intrathecal administration. The present invention also provides methods of treating Hunter syndrome by administering into a subject in need of treatment a purified recombinant I2S, pharmaceutical composition or formulation containing the same.

As used herein, the terms "I2S protein," "I2S," "I2S enzyme," or grammatical equivalents, refer to a preparation of recombinant I2S protein molecules unless otherwise specifically indicated.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Figures described below, that together make up the Drawing, are for illustration purposes only, not for limitation.

DEFINITIONS

Figure 1:
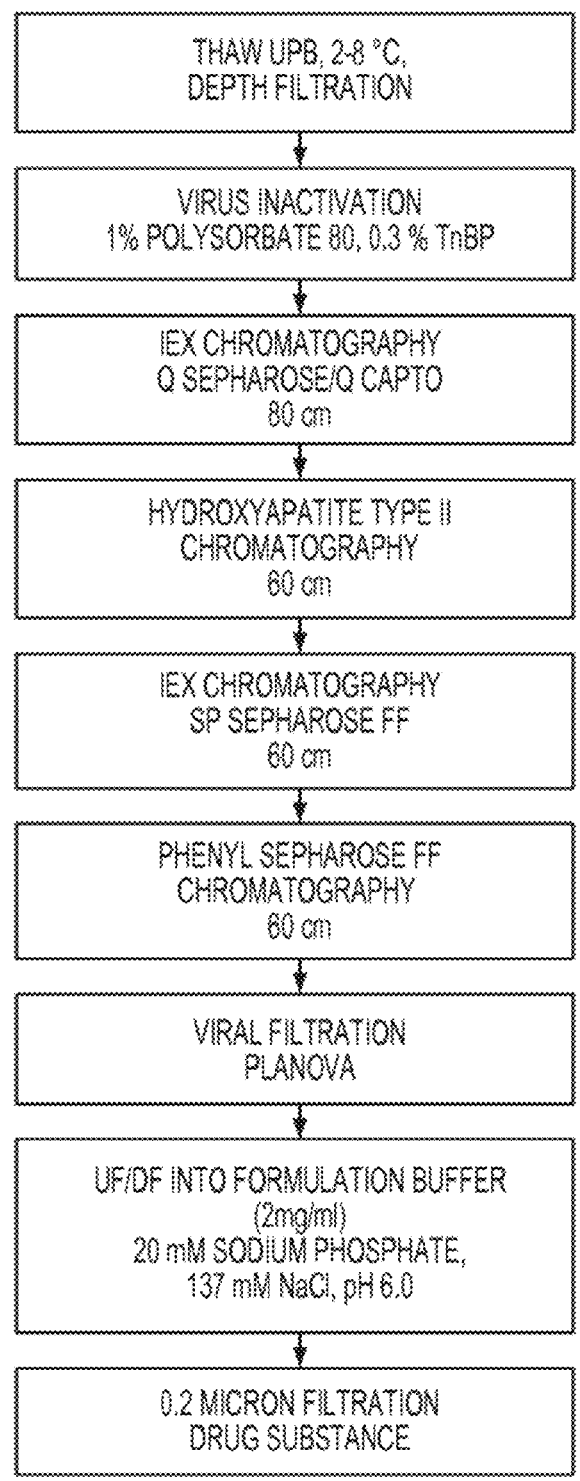
FIG. 1 depicts an exemplary purification scheme for recombinant I2S produced in serum free medium.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays such as sulfate release assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject. In some embodiments, a protein requires further processing in order to become biologically active. In some embodiments, a protein requires post-translational modification such as, but is not limited to, glycosylation (e.g., sialyation), farnysylation, cleavage, folding, formylglycine conversion and combinations thereof, in order to become biologically active. In some embodiments, a protein produced as a proform (i.e. immature form), may require additional modification to become biologically active.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Chromatography: As used herein, the term "chromatography" refers to a technique for separation of mixtures. Typically, the mixture is dissolved in a fluid called the "mobile phase," which carries it through a structure holding another material called the "stationary phase." Column chromatography is a separation technique in which the stationary bed is within a tube, i.e., column.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Elution: As used herein, the term "elution" refers to the process of extracting one material from another by washing with a solvent. For example, in ion-exchange chromatography, elution is a process to wash loaded resins to remove captured ions.

Eluate: As used herein, the term "eluate" refers to a combination of mobile phase "carrier" and the analyte material that emerge from the chromatography, typically as a result of eluting.

Enzyme replacement therapy (ERT): As used herein, the term "enzyme replacement therapy (ERT)" refers to any therapeutic strategy that corrects an enzyme deficiency by providing the missing enzyme. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Equilibrate or Equilibration: As used herein, the terms "equilibrate" or "equilibration" in relation to chromatography refer to the process of bringing a first liquid (e.g., buffer) into balance with another, generally to achieve a stable and equal distribution of components of the liquid (e.g., buffer). For example, in some embodiments, a chromatographic column may be equilibrated by passing one or more column volumes of a desired liquid (e.g., buffer) through the column.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Impurities: As used herein, the term "impurities" refers to substances inside a confined amount of liquid, gas, or solid, which differ from the chemical composition of the target material or compound. Impurities are also referred to as contaminants.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Load: As used herein, the term "load" refers to, in chromatography, adding a sample-containing liquid or solid to a column. In some embodiments, particular components of the sample loaded onto the column are then captured as the loaded sample passes through the column. In some embodiments, particular components of the sample loaded onto the column are not captured by, or "flow through", the column as the loaded sample passes through the column.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Pool: As used herein, the term "pool" in relation to chromatography refers to combining one or more fractions of fluid that has passed through a column together. For example, in some embodiments, one or more fractions which contain a desired component of a sample that has been separated by chromatography (e.g., "peak fractions") can be "pooled" together generate a single "pooled" fraction.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, therapeutic agents in accordance with the present invention are soluble in its corresponding pharmaceutical composition.

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Viral Processing: As used herein, the term "viral processing" refers to "viral removal," in which viruses are simply removed from the sample, or "viral inactivation," in which the viruses remain in a sample but in a non-infective form. In some embodiments, viral removal may utilize nanofiltration and/or chromatographic techniques, among others. In some embodiments, viral inactivation may utilize solvent inactivation, detergent inactivation, pasteurization, acidic pH inactivation, and/or ultraviolet inactivation, among others.

DETAILED DESCRIPTION OF THE INVENTION

The present invention provides, among other things, an improved method for purifying recombinant I2S protein for enzyme replacement therapy based on a process involving less than 6 chromatography steps. In some embodiments, the present invention provides a method of purifying recombinant I2S protein from an impure preparation using a process based on one or more of anion-exchange chromatography, cation-exchange chromatography, mixed-mode chromatography, and hydrophobic interaction chromatography. In some embodiments, the present invention provides a method of purifying recombinant I2S protein from an impure preparation by conducting Q chromatography, hydroxyapatite (HA) chromatography, SP chromatography, and phenyl chromatography. The present invention further provides purified recombinant I2S protein and method of use.

Various aspects of the invention are described in further detail in the following subsections. The use of subsections is not meant to limit the invention. Each subsection may apply to any aspect of the invention. In this application, the use of "or" means "and/or" unless stated otherwise.

Recombinant I2S Protein

As used herein, an I2S protein is any protein or a portion of a protein that can substitute for at least partial activity of naturally-occurring Iduronate-2-sulfatase (I2S) protein or rescue one or more phenotypes or symptoms associated with I2S-deficiency. As used herein, the terms "an I2S enzyme" and "an I2S protein", and grammatical equivalents, are used inter-changeably.

Typically, the human I2S protein is produced as a precursor form. The precursor form of human I2S contains a signal peptide (amino acid residues 1-25 of the full length precursor), a pro-peptide (amino acid residues 26-33 of the full length precursor), and a chain (residues 34-550 of the full length precursor) that may be further processed into the 42 kDa chain (residues 34-455 of the full length precursor) and the 14 kDa chain (residues 446-550 of the full length precursor). Typically, the precursor form is also referred to as full-length precursor or full-length I2S protein, which contains 550 amino acids. The amino acid sequences of the mature form (SEQ ID NO:1) having the signal peptide removed and full-length precursor (SEQ ID NO: 2) of a typical wild-type or naturally-occurring human I2S protein are shown in Table 1. The signal peptide is underlined. In addition, the amino acid sequences of human I2S protein isoform a and b precursor are also provided in Table 1, SEQ ID NO:3 and 4, respectively.

TABLE 1

Human Iduronate-2-sulfatase

| | |
|---|---|
| Mature Form | SETQANSTTDALNVLLIIVDDLRPSLGCYGDKLVRSPNIDQLASHSLLFQNAF<br>AQQAVCAPSRVSFLTGRRPDTTRLYDENSYWRVHAGNESTIPQYFKENGYVTM<br>SVGKVFHPGISSNHTDDSPYSWSFPPYHPSSEKYENTKTCRGPDGELHANLLC<br>PVDVLDVPEGTLPDKQSTEQAIQLLEKMKTSASPFFLAVGYHKPHIPFRYPKE<br>FQKLYPLENITLAPDPEVPDGLPPVAYNPWMDIRQREDVQALNISVPYGPIPV<br>DFQRKIRQSYFASVSYLDTQVGRLLSALDDLQLANSTIIAFTSDHGWALGEHG<br>EWAKYSNFDVATHVPLIFYVPGRTASLPEAGEKLFPYLDPFDSASQLMEPGRQ<br>SMDLVELVSLFPTLAGLAGLQVPPRCPVPSFHVELCREGKNLLKHFRFRDLEE<br>DPYLPGNPRELIAYSQYPRPSDIPQWNSDKPSLKDIKIMGYSIRTIDYRYTVW<br>VGFNPDEFLANFSDIHAGELYFVDSDPLQDHNMYNDSQGGDLFQLLMP (SEQ<br>ID NO: 1) |
| Full-Length<br>Precursor<br>(Isoform a) | MPPPRTGRGLLWLGLVLSSVCVALGSETQANSTTDALNVLLIIVDDLRPSLGC<br>YGDKLVRSPNIDQLASHSLLFQNAFAQQAVCAPSRVSFLTGRRPDTTRLYDEN<br>SYWRVHAGNFSTIPQYFKENGYVTMSVGKVFHPGISSNHTDDSPYSWSFPPYH<br>PSSEKYENTKTCRGPDGELHANLLCPVDVLDVPEGTLPDKQSTEQAIQLLEKM<br>KTSASPFFLAVGYHKPHIPFRYPKEFQKLYPLENITLAPDPEVPDGLPPVAYN<br>PWMDIRQREDVQALNISVPYGPIPVDFQRKIRQSYFASVSYLDTQVGRLLSAL<br>DDLQLANSTIIAFTSDHGWALGEHGEWAKYSNFDVATHVPLIFYVPGRTASLP<br>EAGEKLFPYLDPFDSASQLMEPGRQSMDLVELVSLFPTLAGLAGLQVPPRCPV<br>PSFHVELCREGKNLLKHFRFRDLEEDPYLPGNPRELIAYSQYPRPSDIPQWNS<br>DKPSLKDIKIMGYSIRTIDYRYTVWVGFNPDEFLANFSDIHAGELYFVDSDPL<br>QDHNMYNDSQGGDLFQLLMP (SEQ ID NO: 2) |
| Isoform b<br>Precursor | MPPPRTGRGLLWLGLVLSSVCVALGSETQANSTTDALNVLLIIVDDLRPSLGC<br>YGDKLVRSPNIDQLASHSLLFQNAFAQQAVCAPSRVSFLTGRRPDTTRLYDEN<br>SYWRVHAGNFSTIPQYFKENGYVTMSVGKVFHPGISSNHTDDSPYSWSFPPYH<br>PSSEKYENTKTCRGPDGELHANLLCPVDVLDVPEGTLPDKQSTEQAIQLLEKM<br>KTSASPFFLAVGYHKPHIPFRYPKEFQKLYPLENITLAPDPEVPDGLPPVAYN<br>PWMDIRQREDVQALNISVPYGPIPVDFQEDQSSTGFRLKTSSTRKYK (SEQ<br>ID NO: 3) |
| Isoform c<br>Precursor | MPPPRTGRGLLWLGLVLSSVCVALGSETQANSTTDALNVLLIIVDDLRPSLGC<br>YGDKLVRSPNIDQLASHSLLFQNAFAQQAVCAPSRVSFLTGRRPDTTRLYDEN<br>SYWRVHAGNFSTIPQYFKENGYVTMSVGKVFHPGISSNHTDDSPYSWSFPPYH<br>PSSEKYENTKTCRGPDGELHANLLCPVDVLDVPEGTLPDKQSTEQAIQLLEKM<br>KTSASPFFLAVGYHKPHIPFRYPKEFQKLYPLENITLAPDPEVPDGLPPVAYN<br>PWMDIRQREDVQALNISVPYGPIPVDFQRKIRQSYFASVSYLDTQVGRLLSAL<br>DDLQLANSTIIAFTSDHGELMRTNT (SEQ ID No : 4) |

Thus, in some embodiments, a recombinant I2S protein is mature human I2S protein (SEQ ID NO:1). As disclosed herein, SEQ ID NO:1 represents the canonical amino acid sequence for the human I2S protein. In some embodiments, the I2S protein may be a splice isoform and/or variant of SEQ ID NO:1, resulting from transcription at an alterative start site within the 5' UTR of the I2S gene. In some embodiments, a recombinant I2S protein may be a homologue or an analogue of mature human I2S protein. For example, a homologue or an analogue of mature human I2S protein may be a modified mature human I2S protein containing one or more amino acid substitutions, deletions, and/or insertions as compared to a wild-type or naturally-occurring I2S protein (e.g., SEQ ID NO:1), while retaining substantial I2S protein activity. Thus, in some embodiments, a recombinant I2S protein is substantially homologous to mature human I2S protein (SEQ ID NO:1). In some embodiments, a recombinant I2S protein has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a recombinant I2S protein is substantially identical to mature human I2S protein (SEQ ID NO:1). In some embodiments, a recombinant I2S protein has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a recombinant I2S protein contains a fragment or a portion of mature human I2S protein.

Alternatively, a recombinant I2S protein is full-length I2S protein. In some embodiments, a recombinant I2S protein may be a homologue or an analogue of full-length human I2S protein. For example, a homologue or an analogue of full-length human I2S protein may be a modified full-length human I2S protein containing one or more amino acid substitutions, deletions, and/or insertions as compared to a wild-type or naturally-occurring full-length I2S protein (e.g., SEQ ID NO:2), while retaining substantial I2S protein activity. Thus, In some embodiments, a recombinant I2S protein is substantially homologous to full-length human I2S protein (SEQ ID NO:2). For example, a recombinant I2S protein may have an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a recombinant I2S protein is substantially identical to SEQ ID NO:2. For example, a recombinant I2S protein may have an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 2. In some embodiments, a recombinant I2S protein contains a fragment or a portion of full-length human I2S protein. As used herein, a full-length I2S protein typically contains signal peptide sequence.

In some embodiments, a recombinant I2S protein is human I2S isoform a protein. In some embodiments, a recombinant I2S protein may be a homologue or an analogue of human I2S isoform a protein. For example, a homologue or an analogue of human I2S isoform a protein may be a modified human I2S isoform a protein containing one or more amino acid substitutions, deletions, and/or insertions as compared to a wild-type or naturally-occurring human I2S isoform a protein (e.g., SEQ ID NO:3), while retaining substantial I2S protein activity. Thus, in some embodiments, a recombinant I2S protein is substantially homologous to human I2S isoform a protein (SEQ ID NO:3). For example, a recombinant I2S protein may have an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:3. In some embodiments, a recombinant I2S protein is substantially identical to SEQ ID NO:3. For example, a recombinant I2S protein may have an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 3. In some embodiments, a recombinant I2S protein contains a fragment or a portion of human I2S isoform a protein. As used herein, a human I2S isoform a protein typically contains a signal peptide sequence.

In some embodiments, a recombinant I2S protein is human I2S isoform b protein. In some embodiments, a recombinant I2S protein may be a homologue or an analogue of human I2S isoform b protein. For example, a homologue or an analogue of human I2S isoform b protein may be a modified human I2S isoform b protein containing one or more amino acid substitutions, deletions, and/or insertions as compared to a wild-type or naturally-occurring human I2S isoform b protein (e.g., SEQ ID NO:4), while retaining substantial I2S protein activity. Thus, in some embodiments, a recombinant I2S protein is substantially homologous to human I2S isoform b protein (SEQ ID NO:4). For example, a recombinant I2S protein may have an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a recombinant I2S protein is substantially identical to SEQ ID NO:4. For example, a recombinant I2S protein may have an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4. In some embodiments, a recombinant I2S protein contains a fragment or a portion of human I2S isoform b protein. As used herein, a human I2S isoform b protein typically contains a signal peptide sequence.

Homologues or analogues of human I2S proteins can be prepared according to methods for altering polypeptide sequence known to one of ordinary skill in the art such as are found in references that compile such methods. In some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. In some embodiments, a "conservative amino acid substitution" refers to an amino acid substitution that does not alter the relative charge or size characteristics of the protein in which the amino acid substitution is made.

In some embodiments, recombinant I2S proteins may contain a moiety that binds to a receptor on the surface of target cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a recombinant I2S protein contains M6P residues on the surface of the protein. In particular, a recombinant I2S protein may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme.

In some embodiments, recombinant I2S enzymes may be fused to a lysosomal targeting moiety that is capable of binding to a receptor on the surface of target cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence). The lysosomal targeting moiety may be conjugated or fused to an I2S protein or enzyme at the N-terminus, C-terminus or internally.

Production of Recombinant I2S Proteins

The present invention may be used to purify a recombinant I2S protein produced by various means. For example, an I2S protein may be recombinantly produced by utilizing a host cell system engineered to express an I2S-encoding nucleic acid. Alternatively, an I2S protein may be produced by activating an endogenous I2S gene.

It is contemplated that the present invention can be used to purify a recombinant I2S protein produced using various expression system. Suitable expression systems include, for example, egg, baculovirus, plant, yeast, or mammalian cells.

In some embodiments, I2S enzymes are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (HEK293 or 293 cells subcloned for growth in suspension culture, Graham et al., J. Gen Virol., 36:59,1977); human fibrosarcoma cell line (e.g., HT1080); baby hamster kidney cells (BHK21, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to purify recombinant I2S enzymes produced from human cells (e.g., HT1080). In some embodiments, inventive methods according to the present invention are used to purify recombinant I2S enzymes produced from CHO cells.

Typically, cells that are engineered to express recombinant I2S may comprise a transgene that encodes a recombinant I2S protein described herein. It should be appreciated that the nucleic acids encoding recombinant I2S may contain regulatory sequences, gene control sequences, promoters, non-coding sequences and/or other appropriate sequences for expressing the recombinant I2S. Typically, the coding region is operably linked with one or more of these nucleic acid components.

"Regulatory sequences" typically refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. Sometimes, "regulatory sequences" are also referred to as "gene control sequences."

"Promoter" typically refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" typically refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" or "5' non-coding sequences" typically refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

Typically, the term "operatively linked" or "operably linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a transgene may include one or more silent mutations to optimize codon usage for a particular cell type. For example, the codons of an I2S transgene may be optimized for expression in a vertebrate cell. In some embodiments, the codons of an I2S transgene may be optimized for expression in a mammalian cell. In some embodiments, the codons of an I2S transgene may be optimized for expression in a human cell.

Optionally, a construct may contain additional components such as one or more of the following: a splice site, an enhancer sequence, a selectable marker gene under the control of an appropriate promoter, an amplifiable marker gene under the control of an appropriate promoter, and a matrix attachment region (MAR) or other element known in the art that enhances expression of the region where it is inserted.

Once transfected or transduced into host cells, a suitable vector can express extrachromosomally (episomally) or integrate into the host cell's genome.

Activation of Recombinant I2S Proteins

Typically, a recombinant I2S enzyme is activated by the post-translational modification of a conserved cysteine (corresponding to amino acid 59 of mature human I2S) to formylglycine, also known as 2-amino-3-oxopropionic acid, or oxo-alanine. Such post-translational modification can be carried out by an enzyme known as Formylglycine Generating Enzyme (FGE). Thus, in some embodiments, recombinant I2S enzymes are produced in cells that also express FGE protein. In particular embodiments, recombinant I2S enzymes are produced in cells that have increased or enhanced expression of FGE protein. For example, cells may be engineered to over-express FGE in combination with recombinant I2S to facilitate the production of I2S preparations having high levels of active enzyme. In some embodiments, over-expression of FGE is achieved by expression (e.g., over-expression) of an exogenous FGE using standard recombinant technology. In some embodiments, over-expression of FGE is achieved by activated or enhanced expression of an endogenous FGE by, for example, activating or enhancing the promoter of the endogenous FGE gene. In some cases, the nucleic acid encoding recombinant I2S and the nucleic acid encoding a recombinant FGE protein are linked by a nucleic acid (e.g., a spacer sequence) having a sequence corresponding to an internal ribosomal entry site.

Any FGE having ability to convert cysteine to formylglycine may be used in the present invention. Exemplary nucleic acid and amino acid sequences for FGE proteins are disclosed in US 2004-0229250, the entire contents relating to such sequences and the sequences themselves are incorporated herein by reference in their entireties. It should be appreciated that the nucleic acids encoding recombinant FGE may comprise regulatory sequences, gene control sequences, promoters, non-coding sequences and/or other appropriate sequences for expressing the FGE. Typically, the coding region is operably linked with one or more of these nucleic acid components.

Cell Culture Medium and Condition

Various cell culture medium and conditions may be used to produce a recombinant I2S protein. For example, a recombinant I2S protein may be produced in serum-containing or serum-free medium. In some embodiments, a recombinant I2S protein is produced in serum-free medium. In some embodiments, a recombinant I2S protein is produced in an animal free medium, i.e., a medium that lacks animal-derived components. In some embodiments, a recombinant I2S protein is produced in a chemically defined medium. As used herein, the term "chemically-defined nutrient medium" refers to a medium of which substantially all of the chemical components are known. In some embodiments, a chemically defined nutrient medium is free of animal-derived components such as serum, serum derived proteins (e.g., albumin or fetuin), and other components. In some cases, a chemically-defined medium comprises one or more proteins (e.g., protein growth factors or cytokines.) In some cases, a chemically-defined nutrient medium comprises one or more protein hydrolysates. In other cases, a chemically-defined nutrient medium is a protein-free media, i.e., a serum-free media that contains no proteins, hydrolysates or components of unknown composition.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin).

Various cell culture conditions may be used to produce recombinant I2S proteins at large scale including, but not limited to, roller bottle cultures, bioreactor batch cultures and bioreactor fed-batch cultures. In some embodiments, recombinant I2S protein is produced by cells cultured in suspense. In some embodiments, recombinant I2S protein is produced by adherent cells.

Exemplary cell media and culture conditions are described in the Examples sections. Additional exemplary methods and compositions for producing recombinant I2S protein are described in the provisional application entitled "Methods and Compositions for Producing Recombinant Iduronate-2-Sulfatase" filed herewith on even date, the entire disclosure of which is hereby incorporated by reference.

Purification of Recombinant I2S Protein

In some embodiments, the present invention provides a method of purifying recombinant I2S protein from an impure preparation using a process based on one or more of anion-exchange chromatography, cation-exchange chromatography, mixed-mode chromatography, and hydrophobic interaction chromatography. In some embodiments, an inventive method according to the present invention involves less than 6 (e.g., less than 5, less than 4, or less than 3) chromatography steps. In some embodiments, an inventive method according to the present invention involves 2, 3, 4 or 5 chromatography steps. In some embodiments, an inventive method according to the present invention involves 4 chromatography steps. In some embodiments, an inventive method according to the present invention conducts anion-exchange chromatography, mixed-mode chromatography, cation-exchange chromatography, and hydrophobic interaction chromatography in that order.

Impure Preparation

As used herein, an impure preparation can be any biological material including unprocessed biological material containing recombinant I2S protein. For example, an impure preparation may be unprocessed cell culture medium containing recombinant I2S protein secreted from the cells (e.g., mammalian cells) producing I2S protein or raw cell lysates containing I2S protein. In some embodiments, an impure preparation may be partially processed cell medium or cell lysates. For example, cell medium or cell lysates can be concentrated, diluted, treated with viral inactivation, viral processing or viral removal. In some embodiments, viral removal may utilize nanofiltration and/or chromatographic techniques, among others. In some embodiments, viral inactivation may utilize solvent inactivation, detergent inactivation, pasteurization, acidic pH inactivation, and/or ultraviolet inactivation, among others. Cell medium or cell lysates may also be treated with protease, DNases, and/or RNases to reduce the level of host cell protein and/or nucleic acids (e.g., DNA or RNA). In some embodiments, unprocessed or partially processed biological materials (e.g., cell medium or cell lysate) may be frozen and stored at a desired temperature (e.g., 2-8° C., −4° C., −25° C., −75° C.) for a period time and then thawed for purification. As used herein, an impure preparation is also referred to as starting material or loading material.

Anion-Exchange Chromatography

In some embodiments, provided methods for purifying recombinant I2S include anion-exchange chromatography. In brief, anion exchange chromatography is a chromatographic technique which relies on charge-charge interactions between a negatively charged compound and a positively charged resin. In some embodiments, the anion-exchange chromatography is strong anion-exchange chromatography. In some embodiments, anion-exchange chromatography is employed as a first purification step for a therapeutic protein (e.g., recombinant I2S).

Exemplary anion exchange resins include, but are not limited to, quaternary amine resins or "Q-resins" (e.g., Capto™_Q, Q-Sepharose®, QAE Sephadex®); diethylaminocthane (DEAE) resins (e.g., DEAE-Trisacryl®, DEAE Sepharose®, benzoylated naphthoylated DEAE, diethylaminocthyl Sephacel®); Amberjet® resins; Amberlyst® resins; Amberlite® resins (e.g., Amberlite® IRA-67, Amberlite® strongly basic, Amberlite® weakly basic), cholestyramine resin, ProPac® resins (e.g., ProPac® SAX-10, ProPac@ WAX-10, ProPac® WCX-10); TSK-GEL® resins (e.g., TSKgel DEAE-NPR; TSKgel DEAE-5 PW); and Acclaim® resins. In certain embodiments, the anion exchange resin is a Q resin.

Typical mobile phases for anionic exchange chromatography include relatively polar solutions, such as water, acetonitrile, organic alcohols such as methanol, ethanol, and isopropanol, or solutions containing 2-(N-morpholino)-ethanesulfonic acid (MES). Thus, in certain embodiments, the mobile phase includes about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% polar solution. In certain embodiments, the mobile phase comprises between about 1% to about 100%, about 5% to about 95%, about 10% to about 90%, about 20% to about 80%, about 30% to about 70%, or about 40% to about 60% polar solution at any given time during the course of the separation.

Generally, a mobile phase includes a salt. For example, a salt (e.g., sodium chloride) can elute a bound protein from an anion exchange column (e.g., the counter ion is chloride and it is exchanged for the target protein, which is then released). In some embodiments, the mobile phase includes a salt concentration between about 0 to about 1.0M, e.g., between about 0 to about 0.8M, between about 0 to about 0.6M, between about 0 to about 0.5M, between about 0 to about 0.4M, between about 0.05M to about 0.50M, between about 0.10M to about 0.45M, between about 0.10M to about 0.40M, or between about 0.15M to about 0.40M. In some embodiments, the mobile phase includes a salt concentration of approximately 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, or 1.0M. In some embodiments, salt concentration in the mobile phase is a gradient (e.g., linear or non-linear gradient). In some embodiments, salt concentration in the mobile phase is constant. In some embodiments, salt concentration in the mobile phase may increase or decrease stepwise.

Typically, the mobile phase is buffered. In certain embodiments, the mobile phase is not buffered. In certain embodiments, the mobile phase is buffered to a pH between about 5 to about 14. In certain embodiments, the mobile phase is buffered to a pH between about 5 to about 10. In certain embodiments, the mobile phase is buffered to a pH between about 5 to about 7. In certain embodiments, the mobile phase is buffered to a pH of about 6.5. In certain embodiments, the mobile phase is buffered to a pH of about 5.0, 5.5, 6.0, 6.5, 7.0, 7.5, 8.0, 8.5, 9.0, 9.5, or 10.

In some embodiments, an impure preparation or an intermediate eluate or flow-through is adjusted to pH of about 5.0, 5.5, 6.0, 6.5, 7.0 or 7.5 and the conductivity of about 2 mS/cm, 4 mS/cm, 6 mS/cm, 8 mS/cm, 10 mS/cm, 12 mS/cm, 14 mS/cm, 16 mS/cm, 18 mS/cm, or 20 mS/cm prior to loading to the anion-exchange chromatography column (e.g., Q column). The pH may be adjusted using sodium acetate (e.g., 1M) and the conductivity may be adjusted using sodium chloride (e.g., 5M). Once loaded, an anion-exchange chromatography column may be washed using a wash buffer comprising salt (e.g., NaCl) concentration ranging from about 140 mM to about 200 mM (e.g., about 140 mM, 145 mM, 150 mM, 155 mM, 160 mM, 165 mM, 170 mM, 175 mM, 180 mM, 185 mM, 190 mM, 195 mM, or 200 mM) with pH of about 5.0-7.5 (e.g., about 5.0, 5.5, 6.0, 6.5, 7.0 or 7.5). An anion-exchange chromatography column may be eluted using an elution buffer comprising a linear NaCl gradient. A suitable exemplary linear NaCl gradient may contain a range from about 0-500 mM NaCl (e.g., about 0-400 mM, about 0-350 mM, about 0-300 mM, about 50-500 mM, about 150-500 mM, about 150-450 mM, about 150-400 mM).

Cation Exchange Chromatography

In some embodiments, provided methods for purifying recombinant I2S include cation-exchange chromatography. In brief, cation exchange chromatography is a chromatographic technique which relies on charge-charge interactions between a positively charged compound and a negatively charged resin. In some embodiments, the cation-exchange chromatography is strong cation-exchange chromatography.

Cation exchange chromatography is generally practiced with either a strong or weak cation exchange column, containing a sulfonium ion, or with a weak cation exchanger, having usually a carboxymethyl (CM) or carboxylate (CX) functional group. Many suitable cation exchange resins are known in the art and are commercially available and include, but are not limited to SP-Sepharose®, CM Sepharose®; Amberjet® resins; Amberlyst® resins; Amberlite® resins (e.g., Amberlite® IRA120); ProPac® resins (e.g., ProPac® ScX-10, ProPac® WCX-10, ProPac® WCX-10); TSK-GEL® resins (e.g., TSKgel BioAssist S; TSKgel SP-2SW, TSKgel SP-5 PW; TSKgel SP-NPR; TSKgel SCX; TSKgel SP-STAT; TSKgel CM-5 PW; TSKgel OApak-A; TSKgel CM-2SW, TSKgel CM-3SW, and TSKgel CM-STAT); and Acclaim® resins. In certain embodiments, the anion exchange resin is an SP-Sepharose resin®.

Typical mobile phases for cationic exchange chromatography include relatively polar solutions, such as water, acetonitrile, organic alcohols such as methanol, ethanol, and isopropanol, or solutions containing 2-(N-morpholino)-ethanesulfonic acid (MES). Thus, in certain embodiments, the mobile phase includes about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% polar solution. In certain embodiments, the mobile phase includes between about 1% to about 100%, about 5% to about 95%, about 10% to about 90%, about 20% to about 80%, about 30% to about 70%, or about 40% to about 60% polar solution at any given time during the course of the separation.

Generally, a mobile phase includes a salt. For example, a salt (e.g., sodium chloride, sodium phosphate, etc.) can elute a bound protein from an cation exchange column (e.g., the counter ion is sodium and it is exchanged for the target protein, which is then released). In some embodiments, the mobile phase includes a salt concentration between about 0 to about 1.0M, e.g., between about 0 to about 0.8M, between about 0 to about 0.6M, between about 0 to about 0.5M, between about 0 to about 0.4M, between about 0.05M to about 0.50M, between about 0.10M to about 0.45M, between about 0.10M to about 0.40M, or between about 0.15M to about 0.40M. In some embodiments, the mobile phase includes a salt concentration of approximately 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, or 1.0M. In some embodiments, salt concentration in the mobile phase is a gradient (e.g., linear or non-linear gradient). In some embodiments, salt concentration in the mobile phase is constant. In some embodiments, salt concentration in the mobile phase may increase or decrease stepwise.

Typically, the mobile phase is buffered. In certain embodiments, the mobile phase is not buffered. In certain embodiments, the mobile phase is buffered to a pH between about 5 to about 14. In certain embodiments, the mobile phase is buffered to a pH between about 5 to about 10. In certain embodiments, the mobile phase is buffered to a pH between about 5 to about 7. In certain embodiments, the mobile phase is buffered to a pH of about 6.5. In certain embodiments, the mobile phase is buffered to a pH of about 5.0, 5.5, 6.0, 6.5, 7.0, 7.5, 8.0, 8.5, 9.0, 9.5, or 10.

In some embodiments, an impure preparation or an intermediate eluate or flow-through is adjusted to conductivity ranging between about 1 mS/cm and 20 mS/cm (e.g., between about 1 mS/cm and 15 mS/cm, between about 1 mS/cm and 10 mS/cm, between about 1 mS/cm and 8 mS/cm, between about 1 mS/cm and 6 mS/cm, between about 1 mS/cm and 4 mS/cm, between about 2 mS/cm and 4 mS/cm) prior to loading to the cation-exchange chromatography column (e.g., SP column). In particular embodiments, an impure preparation or an intermediate eluate or flow-through is adjusted to conductivity ranging between n about 2 mS/cm and 4 mS/cm (e.g., 2, 2.5, 3, 3.5, or 4 mS/cm) prior to loading to the cation-exchange chromatography column (e.g., SP column). The conductivity may be adjusted by diluting an impure preparation or an intermediate eluate or flow-through with $H_2O$ at, e.g., 1:1, 1.1:1, 1.2:1, 1.3:1, 1.4:1, 1.5:1, 2.0:1, 2.5:1, 3.0:1, 4.0:1, 5.0:1, or 10:1 ratio. The conductivity may also be adjusted by dialfiltration into a desired buffer. In some embodiments, a cation-exchange chromatography column is run at a pH of about 5.0-6.5 (e.g., about 5.0, 5.5, 6.0 or 6.5). In some embodiments, a cation-exchange chromatography column is run with a buffer comprising phosphate (e.g., NaPO4) concentration ranging from about 0.01 M to about 0.1 M (e.g., about 0.01 M, 0.02 M, 0.03 M, 0.04 M, 0.05 M, 0.06 M, 0.07 M, 0.08 M, 0.09 M, or 0.1 M). In some embodiments, a suitable pH is about 5.0-6.5 (e.g., about 5.0, 5.5, 6.0, or 6.5).

Mixed Mode Chromatography

Hydroxyapatite chromatography (HA) is considered to be a "pseudo-affinity" chromatography or "mixed-mode" ion exchange and may be used in accordance with the present invention. Hydroxyapatite is a unique form of calcium phosphate used in fractionation and purification of biological molecules. In some cases, crystalline hydroxyapatite may be used, although the fragility of the crystals may limit flow rates and/or column longetivity. Two types of chemically pure ceramic hydroxyapatite, CHT ceramic hydroxyapatite Types I and II are macroporous, spherical and can be used at high flow rates and pressures. Type I generally has a high protein binding capacity, while Type II generally has a lower binding capacity for proteins. In general, the formula of hydroxyapatite is Cano $(PO_4)_6(OH)_2$ (Kawasaki, et al 1985). The functional groups include positively charged pairs of crystal calcium ions (C-sites) and clusters of six negatively charged oxygen atoms associated with triplets of crystal phosphates (P-sites). C-sites, P-sites and hydroxyls are distributed in a fixed pattern on the crystal surface, generally leading to complex interactions with proteins and other molecules.

A sample may be loaded onto an HA column in low ionic strength phosphate buffer (e.g., 1-10 mM sodium or potassium phosphate) at or near neutral pH. In some embodiments, an impure preparation or an intermediate eluate or flow-through is adjusted to phosphate (e.g., NaPO4) concentration ranging from about 0.001 M to about 0.01 M (e.g., about 0.001 M, 0.002 M, 0.003 M, 0.004 M, 0.005 M, 0.006 M, 0.007 M, 0.008 M, 0.009 M, or 0.01 M) and pH of about 5.0-6.5 (e.g., about 5.0, 5.5, 6.0, or 6.5) prior to loading the mixed-mode chromatography column (e.g., HA column). The loaded HA column are typically washed with a wash buffer having a phosphate concentration comparable to that of the loading buffer. In some embodiments, the mixed-mode chromatography column (e.g., HA column), once loaded, is washed with a wash buffer containing phosphate (e.g., 1-10 mM sodium or potassium phosphate) at or near neutral pH. For example, a suitable wash buffer may have a phosphate concentration of about 1 mM, 2 mM, 3 mM, 4 mM, 5 mM, 6 mM, 7 mM, 8 mM, 9 mM, or 10 mM. In some embodiments, it may be desirable to increase the amount of phosphate in the wash buffer to create a more stringent wash condition. It is contemplated that the M6P levels, in particular di-M6P levels, on the surface of 12S proteins are important for lysosomal targeting. Increased phosphate concentration in the wash buffer may selectively retain 12S proteins with high levels of M6P, in particular, di-M6P on the HA column. Thus, in some embodiments, a desired wash buffer may have a phosphate concentration of or greater than 10 mM, 11 mM, 12 mM, 13 mM, 14 mM, 15 mM, 16 mM, 17 mM, 18 mM, 19 mM, 20 mM. In some embodiments, the loaded mixed-mode chromatography column (e.g., HA column) is washed with a wash buffer having a phosphate concentration ranging from about 10-20 mM (e.g., about 10-18 mM, 10-16 mM, 10-15 mM, 12-20 mM, 14-18 mM, 14-16 mM). In some embodiments, the loaded mixed-mode chromatography column (e.g., HA column) is washed with a wash buffer having a phosphate concentration of or greater than 10 mM, 11 mM, 12 mM, 13 mM, 14 mM, 15 mM, 16 mM, 17 mM, 18 mM, 19 mM, 20 mM.

Elution from an HA column is typically achieved with a gradient phosphate buffer. For example, a suitable elution buffer may have a phosphate gradient of approximately 1-400 mM (e.g., 1-300 mM, 1-200 mM, 1-150 mM, 1-100 mM, 10-350 mM, 10-300 mM, 10-250 mM, 10-200 mM, 10-150 mM, 10-140 mM, 10-130 mM, 10-120 mM, 10-110 mM, 10-100 mM, 10-90 mM, 10-80 mM, 10-70 mM, 10-60 mM, 10-50 mM) sodium phosphate. In some embodiments, elution from an HA column is achieved by stepwise increasing the phosphate concentration in the elution buffer. In some embodiments, stepwise elution buffers may have a phosphate concentration selected from 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 200 mM, 250 mM, 300 mM, 350 mM, 400 mM. In some embodiments, elution from a mixed-mode chromatography column (e.g., HA column) is achieved by an elution buffer having a phosphate (e.g., sodium phosphate) concentration ranging from about 50 mM to about 150 mM (e.g., selected from a phosphate (e.g., sodium phosphate) concentration of about 50 mM, 60 mM, 70 mM, 80 mM, 90 mM, 100 mM, 110 mM, 120 mM, 130 mM, 140 mM, 150 mM, and combination thereof).

It will be appreciated that many different combinations of conditions for HA chromatography are known and may be used to adjust the parameters to be suitable for a particular protein of interest (e.g., recombinant I2S).

Hydrophobic Interaction Chromatography

Hydrophobic Interaction Chromatography (HIC) is a separation technique that uses the properties of hydrophobicity to separate proteins from one another. In this type of chromatography, hydrophobic groups such as phenyl, octyl, or butyl, are attached to the stationary column. Proteins that pass through the column that have hydrophobic amino acid side chains on their surfaces are able to interact with and bind to the hydrophobic groups on the column. HIC columns are known, and include for example, Phenyl Sepharose HIC separations are often designed using the opposite conditions of those used in ion exchange chromatography. In general, a buffer with a high ionic strength, usually ammonium sulfate, is initially applied to the column. The salt in the buffer reduces the solvation of sample solutes thus as solvation decreases, hydrophobic regions that become exposed are adsorbed by the medium. The stationary phase is generally designed to form hydrophobic interactions with other molecules. These interactions are generally too weak in water, however, addition of salts (e.g., $Na_2SO_4$, $K_2SO_4$, $(NH_4)_2SO_4$, NaCl, $NH_4Cl$, NaBr, and NaSCN) to the buffer results in hydrophobic interactions. In some embodiments, the mobile phase includes a salt concentration between about 0.1M to about 3.0M, e.g., between about 0.1M to about 1.5M, between about 0.2M to about 0.8M, or between about 0.3M to about 0.5M.

In certain embodiments, the mobile phase is buffered. In certain embodiments, the mobile phase is not buffered. In certain embodiments, the mobile phase is buffered to a pH between about 5 to about 14. In certain embodiments, the mobile phase is buffered to a pH between about 5 to about 10. In certain embodiments, the mobile phase is buffered to a pH between about 5 to about 7. In certain embodiments, the mobile phase is buffered to a pH of about 5.0.

In some embodiments, an impure preparation or an intermediate eluate or flow-through is adjusted to salt (e.g., NaCl) concentration ranging from about 0.5 M to about 2.0 M (e.g., about 0.5 M, 1.0 M, 1.1 M, 1.2 M, 1.3 M, 1.4 M, 1.5 M, 1.6 M, 1.7 M, 1.8 M, 1.9 M, or 2.0 M) at pH of about 4.5-6.0 (e.g., about 4.5, 5.0, 5.5, or 6.0) prior to loading onto the hydrophobic interaction chromatography column (e.g., phenyl column). Once loaded, a hydrophobic interaction chromatography column may be washed using a wash buffer comprising salt (e.g., NaCl) concentration ranging from about 0.5 M to about 2.0 M (e.g., about 0.5 M, 1.0 M, 1.1 M, 1.2 M, 1.3 M, 1.4 M, 1.5 M, 1.6 M, 1.7 M, 1.8 M, 1.9 M, or 2.0 M) at pH of about 4.5-6.0 (e.g., about 4.5, 5.0, 5.5, or 6.0). In some embodiments, the hydrophobic interaction chromatography column is eluted using a elution buffer comprising salt (e.g., NaCl) concentration ranging from about 0.1 M to about 0.5 M (e.g., about 0.1 M, 0.2 M, 0.3 M, 0.4 M, or 0.5 M) at pH of about 4.5-6.0 (e.g., about 4.5, 5.0, 5.5, or 6.0).

Characterization of Purified 12S Proteins

Purified recombinant I2S protein may be characterized using various methods.

Purity

The purity of purified recombinant I2S protein is typically measure by the level of various impurities (e.g., host cell protein or host cell DNA) present in the final product. For example, the level of host cell protein (HCP) may be measured by ELISA or SDS-PAGE. In some embodiments, the purified recombinant I2S protein contains less than 150 ng HCP/mg I2S protein (e.g., less than 140, 130, 120, 110, 100, 90, 80, 70, 60, 50, 40, 30, 30, 20, 10 ng HCP/mg I2S protein). In some embodiments, the purified recombinant I2S protein, when subject to SDS-PAGE with silver staining, has no new bands with intensity greater than the 0.05%, 0.01%, 0.15%, 0.2%, 0.25%, 0.3%, 0.35%, 0.4%, 0.45%, or 0.5% assay control. Various assay controls may be used, in particular, those acceptable to regulatory agencies such as FDA.

Specific Activity

Purified recombinant I2S protein may also be characterized by evaluating functional and/or biological activity. The enzyme activity of a recombinant I2S composition may be determined using methods known in the art. Typically the methods involve detecting the removal of sulfate from a synthetic substrate, which is known as sulphate release assay. One example of an enzyme activity assay involves the use of ion chromatography. This method quantifies the amount of sulfate ions that are enzymatically released by recombinant I2S from a substrate. The substrate may be a natural substrate or a synthetic substrate. In some cases, the substrate is heparin sulfate (e.g., heparin disaccharide), dermatan sulfate, or a functional equivalent thereof. Typically, the released sulfate ion is analyzed by ion chromatography with a conductivity detector. In this example, the results may be expressed as U/mg of protein where 1 Unit is defined as the quantity of enzyme required to release 1 µmole sulfate ion per hour from the substrate. In some embodiments, purified recombinant I2S protein has a specific activity, as measured by in vitro sulfate release activity assay using heparin disaccharide as substrate, ranging from about 0-100 U/mg, about 10-100 U/mg, about 10-80 U/mg, about 20-80 U/mg. about 20-70 U/mg. about 20-60 U/mg, about 20-50 U/mg, about 30-100 U/mg, about 30-90 U/mg, about 30-80 U/mg, about 30-70 U/mg, about 30-60 U/mg, about 40-100 U/mg, about 40-90 U/mg, about 40-80 U/mg, about 40-70 U/mg, about 40-60 U/mg. In some embodiments, purified recombinant I2S protein has a specific activity, as measured by in vitro sulfate release activity assay using heparin disaccharide as substrate, of at least about 5 U/mg, about 10 U/mg, about 15 U/mg, about 20 U/mg, about 25 U/mg, about 30 U/mg, about 35 U/mg, about 40 U/mg. about 45 U/mg, about 50 U/mg. about 55 U/mg, about 60 U/mg. about 65 U/mg, about 70 U/mg. about 75 U/mg, about 80 U/mg. about 85 U/mg, about 90 U/mg. about 95 U/mg, or about 100 U/mg. Exemplary conditions for performing in vitro sulfate release activity assay using heparin disaccharide as substrate are provided below. Typically, this assay measures the ability of I2S to release sulfate ions from a naturally derived substrate, heparin diasaccharide. The released sulfate may be quantified by ion chromatography. In some cases, ion chromatography is equipped with a conductivity detector. As a non-limiting example, samples are first buffer exchanged to 10 mM Na acetate, pH 6 to remove inhibition by phosphate ions in the formulation buffer. Samples are then diluted to 0.075 mg/ml with reaction buffer (10 mM Na acetate, pH 4.4) and incubated for 2 hrs at 37° C. with heparin disaccharide at an enzyme to substrate ratio of 0.3 ug I2S/100 ug substrate in a 30 uL reaction volume. The reaction is then stopped by heating the samples at 100° C. for 3 min. The analysis is carried out using a Dionex IonPac AS18 analytical column with an IonPac AG18 guard column. An isocratic method is used with 30 mM potassium hydroxide at 1.0 mL/min for 15 minutes. The amount of sulfate released by the I2S sample is calculated from the linear regression analysis of sulfate standards in the range of 1.7 to 16.0 nmoles. The reportable value is expressed as Units per mg protein, where I unit is defined as 1 µmoles of sulfate released per hour and the protein concentration is determined by A280 measurements.

In some embodiments, the enzymatic activity of recombinant I2S protein may also be determined using various other methods known in the art such as, for example, 4-MUF assay which measures hydrolysis of 4-methylumbelliferyl-sulfate to sulfate and naturally fluorescent 4-methylumbelliferone (4-MUF). In some embodiments, a desired enzymatic activity, as measured by in vitro 4-MUF assay, of the produced recombinant I2S protein is at least about 0.5 U/mg, 1.0 U/mg, 1.5 U/mg, 2 U/mg, 2.5 U/mg, 3 U/mg, 4 U/mg, 5 U/mg, 6 U/mg. 7 U/mg, 8 U/mg, 9 U/mg, 10 U/mg, 12 U/mg, 14 U/mg, 16 U/mg, 18 U/mg, or 20 U/mg. In some embodiments, a desired enzymatic activity, as measured by in vitro 4-MUF assay, of the produced recombinant I2S protein ranges from about 0-50 U/mg (e.g., about 0-40 U/mg. about 0-30 U/mg. about 0-20 U/mg. about 0-10 U/mg. about 2-50 U/mg. about 2-40 U/mg. about 2-30 U/mg. about 2-20 U/mg. about 2-10 U/mg. about 4-50 U/mg. about 4-40 U/mg. about 4-30 U/mg. about 4-20 U/mg. about 4-10 U/mg. about 6-50 U/mg. about 6-40 U/mg. about 6-30 U/mg. about 6-20 U/mg. about 6-10 U/mg). Exemplary conditions for performing in vitro 4-MUF assay are provided below. Typically, a 4-MUF assay measures the ability of an I2S protein to hydrolyze 4-methylumbelliferyl-sulfate (4-MUF-$SO_4$) to sulfate and naturally fluorescent 4-methylumbelliferone (4-MUF). One milliunit of activity is defined as the quantity of enzyme required to convert one nanomole of 4-MUF-$SO_4$ to 4-MUF in one minute at 37° C. Typically, the mean fluorescence units (MFU) generated by I2S test samples with known activity can be used to generate a standard curve, which can be used to calculate the enzymatic activity of a sample of interest. Specific activity may then calculated by dividing the enzyme activity by the protein concentration.

In either example, the protein concentration of a recombinant I2S composition may be determined by any suitable method known in the art for determining protein concentrations. In some cases, the protein concentration is determined by an ultraviolet light absorbance assay. Such absorbance assays are typically conducted at about a 280 nm wavelength (A280).

Charge Profile

Purified recombinant I2S may be characterized by the charge profile associated with the protein. Typically, protein charge profile reflects the pattern of residue side chain charges, typically present on the surface of the protein. Charge profile may be determined by performing an ion exchange (IEX) chromatography (e.g., HPLC) assay on the protein. In some embodiments, a "charge profile" refers to a set of values representing the amount of protein that elutes from an ion exchange column at a point in time after addition to the column of a mobile phase containing an exchange ion.

Typically, a suitable ion exchange column is an anion exchange column. For example, a charge profile may be determined by strong anion exchange (SAX) chromatography using a high performance liquid chromatography (HPLC) system. In general, recombinant I2S adsorbs onto the fixed positive charge of a strong anion exchange column and a gradient of increasing ionic strength using a mobile phase at a predetermined flow rate elutes recombinant I2S species from the column in proportion to the strength of their ionic interaction with the positively charged column. More negatively charged (more acidic) I2S species elute later than less negatively charged (less acid) I2S species. The concentration of proteins in the eluate are detected by ultraviolet light absorbance (at 280 nm).

In some embodiments, recombinant I2S adsorbs at about pH 8.0 in 20 mM TRIS-HCl onto the fixed positive charge of a Mini Q PE column and a gradient of increasing ionic strength using a mobile phase consisting of 20 mM TRIS-HCL, 1 M sodium chloride, pH 8.0 at a flow rate of 0.8 ml/min elutes recombinant I2S species from the column in proportion to the strength of their ionic interaction with the positively charged column.

In some embodiments, a charge profile may be depicted by a chromatogram of absorbance units versus time after elution from the HPLC column. The chromatogram may comprise a set of one or more peaks, with each peak in the set identifying a subpopulation of recombinant I2Ss of the composition that have similar surface charges.

Figure 11:
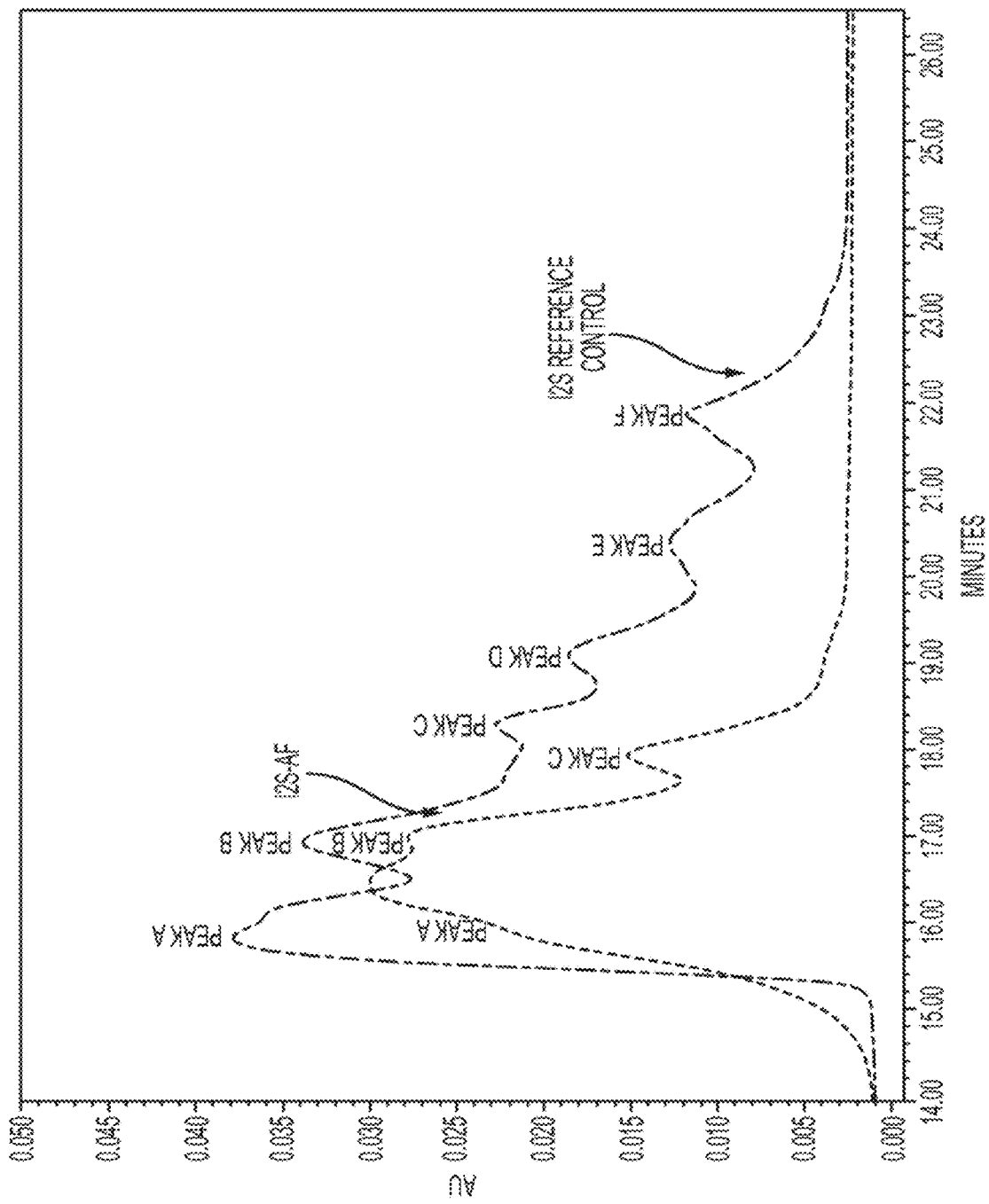
FIG. 11 depicts an exemplary charge profile generated for purified recombinant I2S enzyme produced using the I2S-AF 2D cell line grown under serum-free cell culture conditions as compared to an I2S reference control.

In some embodiments, a purified I2S protein composition exhibits at least six peaks in its charge profile. An exemplary charge profile of I2S is depicted in the Examples section and in FIG. 11. As shown in FIG. 11, six peaks are labeled (A to F) in the order of increasing negative charge and decreasing contribution to total peak area of the chromatogram. In some embodiments, the charge profile for a purified recombinant I2S composition contains a different number, size, shape or time interval of peaks depending on the amount of negative or positive charges on the surface of the protein. In some embodiments, a recombinant I2S composition has a charge profile that has fewer than 6 (e.g., fewer than 5, 4, 3, or 2) peaks. In some embodiments, a charge profile of recombinant I2S may have 5, 4, 3, 2, or 1 peak(s). For example, any one, two, three, four, or five of peaks A, B, C, D, E, and F may be absent or reduced in a purified recombinant I2S protein composition. Typically, a charge profile is considered more homogenous if there are fewer peaks.

Glycan Mapping

In some embodiments, a purified recombinant I2S protein may be characterized by their proteoglycan composition, typically referred to as glycan mapping. Without wishing to be bound by any theory, it is thought that glycan linkage along with the shape and complexity of the branch structure may impact in vivo clearance, lysosomal targeting, bioavailability, and/or efficacy.

Typically, a glycan map may be determined by enzymatic digestion and subsequent chromatographic analysis. Various enzymes may be used for enzymatic digestion including, but not limited to, suitable glycosylases, peptidases (e.g., Endopeptidases, Exopeptidases), proteases, and phosphatases. In some embodiments, a suitable enzyme is alkaline phosphatase. In some embodiments, a suitable enzyme is neuraminidase. Glycans (e.g., phosphoglycans) may be detected by chromatographic analysis. For example, phosphoglycans may be detected by High Performance Anion Exchange Chromatography with Pulsed Amperometric Detection (HPAE-PAD) or size exclusion High Performance Liquid Chromatography (HPLC). The quantity of glycan (e.g., phosphoglycan) represented by each peak on a glycan map may be calculated using a standard curve of glycan (e.g., phosphoglycan), according to methods known in the art and disclosed herein.

Figure 10:
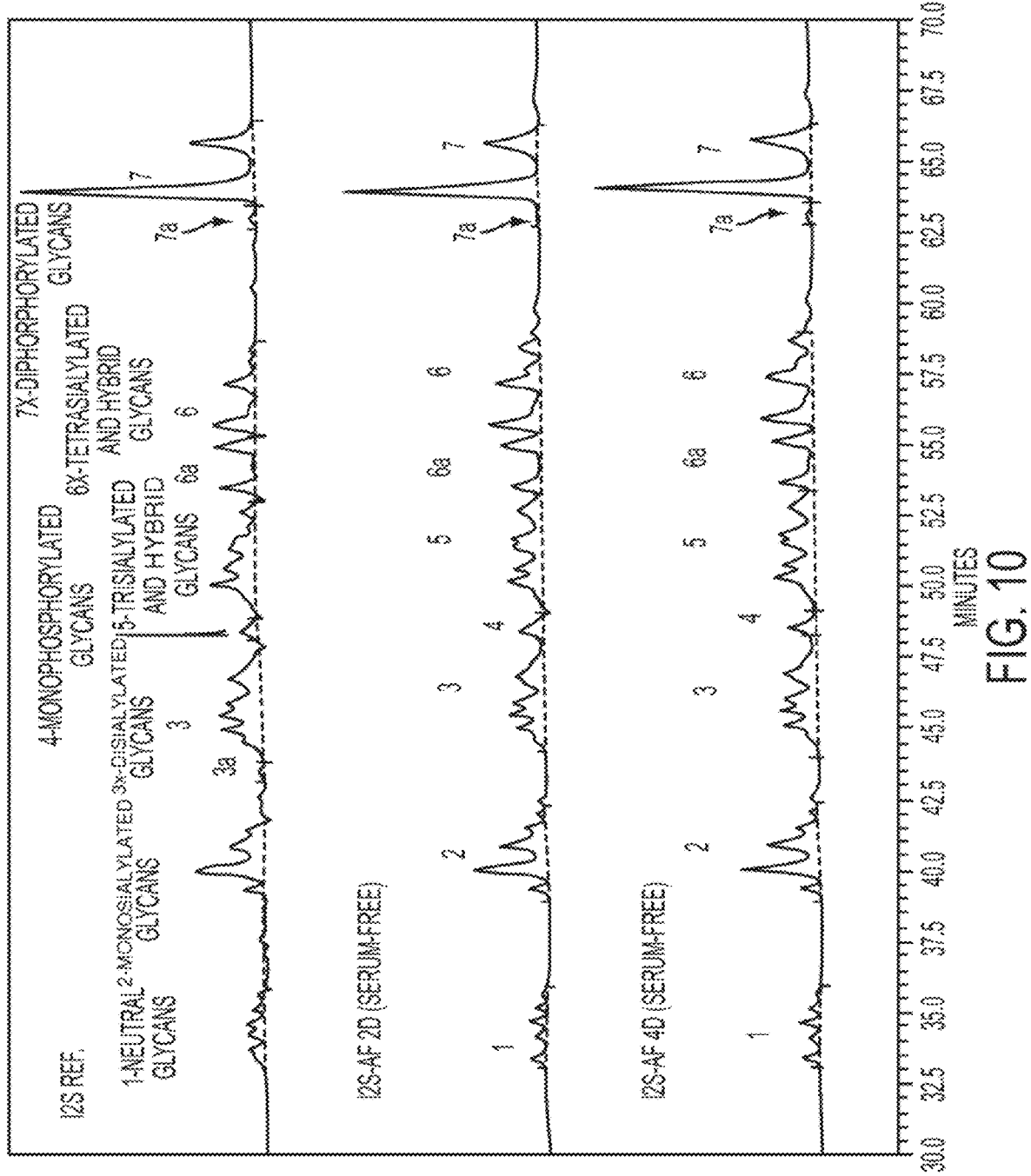
FIG. 10 depicts exemplary glycan profiles generated for purified recombinant I2S enzymes produced using the I2S-AF 2D and 4D cell lines grown under serum-free cell culture conditions as compared to a reference.

In some embodiments, a purified I2S according to the present invention exhibits a glycan map comprising seven peak groups indicative of neutral (peak group 1), monosialylated (peak group 2), di-sialylated (peak group 3), monophosphorylated (peak group 4), tri-sialylated (peak group 5), tetra-sialylated (peak group 6), and diphosphorylated (peak group 7) I2S protein, respectively. Exemplary glycan maps of I2S are depicted in FIG. 10. In some embodiments, a purified recombinant I2S has a glycan map that has fewer than 7 peak groups (e.g., a glycan map with 6, 5, 4, 3, or 2 peaks groups). In some embodiments, a purified recombinant I2S has a glycan map that has more than 7 peak groups (e.g., 8, 9, 10, 11, 12 or more).

The relative amount of glycan corresponding to each peak group may be determined based on the peak group area relative to the corresponding peak group area in a predetermined reference standard. In some embodiments, peak group 1 (neutral) may have the peak group area ranging from about 40-120% (e.g., about 40-115%, about 40-110%, about 40-100%, about 45-120%, about 45-115%, about 45-110%, about 45-105%, about 45-100%, about 50-120%, about 50-110%) relative to the corresponding peak group area in a reference standard. In some embodiments, peak group 2 (monosialylated) may have the peak group area ranging from about 80-140% (e.g., about 80-135%, about 80-130%, about 80-125%, about 90-140%, about 90-135%, about 90-130%, about 90-120%, about 100-140%) relative to the corresponding peak group area in the reference standard. In some embodiments, peak group 3 (disialylated) may have the peak group area ranging from about 80-110% (e.g., about 80-105%, about 80-100%, about 85-105%, about 85-100%) relative to the corresponding peak group area in the reference standard. In some embodiments, peak group 4 (monophosphorylated) may have the peak group area ranging from about 100-550% (e.g., about 100-525%, about 100-500%, about 100-450%, about 150-550%, about 150-500%, about 150-450%, about 200-550%, about 200-500%, about 200-450%, about 250-550%, about 250-500%, about 250-450%, or about 250-400%) relative to the corresponding peak group area in the reference standard. In some embodiments, peak group 5 (tri-sialylated) may have the peak group area ranging from about 70-110% (e.g., about 70-105%, about 70-100%, about 70-95%, about 70-90%, about 80-110%, about 80-105%, about 80-100%, or about 80-95%) relative to the corresponding peak group area in the reference standard. In some embodiments, peak group 6 (tetra-sialylated) may have the peak group area ranging from about 90-130% (e.g., about 90-125%, about 90-120%, about 90-115%, about 90-110%, about 100-130%, about 100-125%, or about 100-120%) relative to the corresponding peak group area in the reference standard. In some embodiments, peak group 7 (diphosphorylated) may have with the peak group area ranging from about 70-130% (e.g., about 70-125%, about 70-120%, about 70-115%, about 70-110%, about 80-130%, about 80-125%, about 80-120%, about 80-115%, about 80-110%, about 90-130%, about 90-125%, about 90-120%, about 90-115%, about 90-110%) relative to the corresponding peak group area in the reference standard. Various reference standards for glycan mapping are known in the art and can be used to practice the present invention. Typically, peak group 7 (diphosphorylated) corresponds to the level of di-M6P on the surface of the purified recombinant I2S protein.

It is contemplated that the glycosylation pattern of a purified I2S impacts the lysosomal targeting. Various in vitro cellular uptake assays are known in the art and can be used to practice the present invention. For example, to evaluate the uptake of I2S by M6P receptors, cellular uptake assays are performed using human fibroblasts expressing M6P receptors on their surface. The internalized amount of I2S can be measured by a ELISA method. In some embodiments, a purified recombinant I2S protein according to the present invention is characterized with cellular uptake of greater than 70%, 75%, 80%, 85%, 90%, 95%, as determined by an in vitro uptake assay.

Peptide Mapping

In some embodiments, peptide mapping may ne used to characterize amino acid composition, post-translational modifications, and/or cellular processing; such as cleavage of a signal peptide, formylglycine conversion and/or glycosylation. Typically, a recombinant protein may be broken into discrete peptide fragments, either through controlled or random breakage, to produce a pattern or peptide map. In some cases, a purified I2S protein may be first subjected to enzymatic digest prior to analytic analysis. Digestion may be performed using a peptidase, glycoside hydrolase, phosphatase, lipase or protease and/or combinations thereof, prior to analytic analysis. The structural composition of peptides may be determined using methods well known in the art. Exemplary methods include, but are not limited to, Mass spectrometry, Nuclear Magnetic Resonance (NMR) or HPLC.

Percent Formylglycine Conversion

Peptide mapping can be used to determine Percent FGly conversion. As discussed above, I2S activation requires Cysteine (corresponding to position 59 of the mature human I2S) to formylglycine conversion by formylglycine generating enzyme (FGE) as shown below:

Therefore, the percentage of formylglycine conversion (% FG) can be calculated using the following formula:

$$\%FG\,(\text{of } DS) = \frac{\text{Number of active } I2S \text{ molecules}}{\text{Number of total (active + inactive) } I2S \text{ molecules}} \times 100$$

To calculate % FG, a recombinant I2S protein may be digested into short peptides using a protease (e.g., trypsin or chymotrypsin). Short peptides may be separated and characterized using, e.g., size exclusion High Performance Liquid Chromatography (HPLC). The peptide containing the position corresponding to position 59 of the mature human I2S may be characterized to determine if the Cys at position 59 was converted to a FGly as compared to a control (e.g., an I2S protein without FGly conversion or an I2S protein with 100% FGly conversion). The amount of peptides containing FGly (corresponding to number of active I2S molecules) and the total amount of peptides with both FGly and Cys (corresponding to number of total I2S molecules) may be determined based on the corresponding peak areas and the ratio reflecting % FG can be calculated.

In some embodiments, a purified recombinant I2S protein according to the present invention has at least about 70% (e.g., at least about 77%, 80%, 85%, 90%, 95%, 96%, 97%, 98%, 99%) conversion of the cysteine residue corresponding to Cys59 of human I2S (SEQ ID NO: 1) to Ca-formylglycine (FGly). In some embodiments, a purified recombinant I2S protein according to the present invention has substantially 100% conversion of the cysteine residue corresponding to Cys59 of human I2S (SEQ ID NO:1) to Ca-formylglycine (FGly).

Sialic Acid Content

In some embodiments, a purified recombinant I2S protein may be characterized by their sialic acid composition. Without wishing to be bound by theory, it is contemplated that sialic acid residues on proteins may prevent, reduce or inhibit their rapid in vivo clearance via the asialoglycoprotein receptors that are present on hepatocytes. Thus, it is thought that recombinant proteins that have relatively high sialic acid content typically have a relatively long circulation time in vivo.

In some embodiments, the sialic acid content of a purified recombinant I2S protein may be determined using methods well known in the art. For example, the sialic acid content of a recombinant I2S protein may be determined by enzymatic digestion and subsequent chromatographic analysis. Enzymatic digestion may be accomplished using any suitable sialidase. In some cases, the digestion is performed by a glycoside hydrolase enzyme, such as neuraminidase. Sialic acid may be detected by chromatographic analysis such as, for example, High Performance Anion Exchange Chromatography with Pulsed Amperometric Detection (HPAE-PAD). The quantity of sialic acid in a recombinant I2S composition may be calculated using a standard curve of sialic acid, according to methods known in the art and disclosed herein.

In some embodiments, the sialic acid content of a purified recombinant I2S protein may be greater than 16 mol/mol. The units "mol/mol" in the context of sialic acid content refers to moles of sialic acid residue per mole of enzyme. In some cases, the sialic acid content of a recombinant I2S protein is or greater than about 16.5 mol/mol, about 17 mol/mol, about 18 mol/mol, about 19 mol/mol, about 20 mol/mol, about 21 mol/mol, about 22 mol/mol or more. In some embodiments, the sialic acid content of a purified recombinant I2S protein may be in a range between about 16-20 mol/mol, 16-21 mol/mol, about 16-22 mol/mol, 16-23 mol/mol, 16-24 mol/mol, about 16-25 mol/mol, about 17-20 mol/mol, 17-21 mol/mol, about 17-22 mol/mol, 17-23 mol/mol, 17-24 mol/mol, or about 17-25 mol/mol.

Pharmaceutical Composition and Administration

Purified recombinant I2S protein may be administered to a Hunter Syndrome patient in accordance with known methods. For example, purified recombinant I2S protein may be delivered intravenously, subcutaneously, intramuscularly, parenterally, transdermally, or transmucosally (e.g., orally or nasally)).

In some embodiments, a recombinant I2S or a pharmaceutical composition containing the same is administered to a subject by intravenous administration.

In some embodiments, a recombinant I2S or a pharmaceutical composition containing the same is administered to a subject by intrathecal administration. As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-SI region of the spine.

In some embodiments, a recombinant I2S or a pharmaceutical composition containing the same is administered to the subject by subcutaneous (i.e., beneath the skin) administration. For such purposes, the formulation may be injected using a syringe. However, other devices for administration of the formulation are available such as injection devices (e.g., the Inject-case™ and Genject™ devices); injector pens (such as the GenPen™); needleless devices (e.g., MediJector™ and BioJector™); and subcutaneous patch delivery systems.

In some embodiments, intrathecal administration may be used in conjunction with other routes of administration (e.g., intravenous, subcutaneously, intramuscularly, parenterally, transdermally, or transmucosally (e.g., orally or nasally)).

The present invention contemplates single as well as multiple administrations of a therapeutically effective amount of a recombinant I2S or a pharmaceutical composition containing the same described herein. A recombinant I2S or a pharmaceutical composition containing the same can be administered at regular intervals, depending on the nature, severity and extent of the subject's condition (e.g., a lysosomal storage disease). In some embodiments, a therapeutically effective amount of a recombinant I2S or a pharmaceutical composition containing the same may be administered periodically at regular intervals (e.g., once every year, once every six months, once every five months, once every three months, bimonthly (once every two months), monthly (once every month), biweekly (once every two weeks), weekly, daily or continuously).

A recombinant 12S or a pharmaceutical composition containing the same can be formulated with a physiologically acceptable carrier or excipient to prepare a pharmaceutical composition. The carrier and therapeutic agent can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to case pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

As used herein, the term "therapeutically effective amount" is largely determined base on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Additional exemplary pharmaceutical compositions and administration methods are described in PCT Publication WO2011/163649 entitled "Methods and Compositions for CNS Delivery of Iduronate-2-Sulfatase;" and provisional application Ser. No. 61/618,638 entitled "Subcutaneous administration of iduronate 2 sulfatase" filed on Mar. 30, 2012, the entire disclosures of both of which are hereby incorporated by reference.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

EXAMPLES

Example 1: Recombinant I2S AF Capture and Purification Process

This example demonstrates a simplified downstream purification process may be used to capture and purify recombinant I2S produced in serum-free medium. An exemplary purification scheme is depicted in FIG. 1.

A cell line stably expressing an iduronate-2-sulfatase enzyme (I2S) and formylglycine generating enzyme (FGE) was developed. Generation and characterization of exemplary cell lines are described in the U.S. Provisional Application entitled "Cells for Producing Recombinant Iduronate-2-Sulfatase" filed on even date herewith, the entire contents of which is hereby incorporated by reference. Briefly, a human cell line was engineered to co-express human I2S protein with the amino acid sequence shown in SEQ ID NO:2 and human formylglycine generating enzyme (FGE) with the amino acid sequence shown in SEQ ID NO:6.

```
>Full-lenth Precursor iduronate 2-sulfatase
                                      SEQ ID NO: 2
MPPPRTGRGLLWLGLVLSSVCVALGSETQANSTTDALNVLLIIVDDLRP
SLGCYGDKLVRSPNIDQLASHSLLFQNAFAQQAVCAPSRVSFLTGRRPD
TTRLYDFNSYWRVHAGNFSTIPQYFKENGYVTMSVGKVFHPGISSNHTD
DSPYSWSFPPYHPSSEKYENTKTCRGPDGELHANLLCPVDVLDVPEGTL
PDKQSTEQAIQLLEKMKTSASPFFLAVGYHKPHIPFRYPKEFQKLYPLE
NITLAPDPEVPDGLPPVAYNPWMDIRQREDVQALNISVPYGPIPVDFQR
KIRQSYFASVSYLDTQVGRLLSALDDLQLANSTIIAFTSDHGWALGEHG
EWAKYSNFDVATHVPLIFYVPGRTASLPEAGEKLFPYLDPFDSASQLME
PGRQSMDLVELVSLFPTLAGLAGLQVPPRCPVPSFHVELCREGKNLLKH
FRFRDLEEDPYLPGNPRELIAYSQYPRPSDIPQWNSDKPSLKDIKIMGY
SIRTIDYRYTVWVGFNPDEFLANFSDIHAGELYFVDSDPLQDHNMYNDS
QGGDLFQLLMP Full-length human FGE precursor:
                                      SEQ ID NO: 6
MAAPALGLVCGRCPELGLVLLLLLLSLLCGAAGSQEAGTGAGAGSLAGS
CGCGTPQRPGAHGSSAAAHRYSREANAPGPVPGERQLAHSKMVPIPAGV
FTMGTDDPQIKQDGEAPARRVTIDAFYMDAYEVSNTEFEKFVNSTGYLT
EAEKFGDSFVFEGMLSEQVKTNIQQAVAAAPWWLPVKGANWRHPEGPDS
TILHRPDHPVLHVSWNDAVAYCTWAGKRLPTEAEWEYSCRGGLHNRLFP
WGNKLQPKGQHYANIWQGEFPVTNTGEDGFQGTAPVDAFPPNGYGLYNI
VGNAWEWTSDWWTVHHSVEETLNPKGPPSGKDRVKKGGSYMCHRSYCYR
YRCAARSQNTPDSSASNLGFRCAADRLPTMD
```

After synthesis of the full length I2S enzyme, the 25 amino acid signal peptide is removed and a soluble mature I2S enzyme is secreted from the cell.

A chemically defined media (serum free/animal-component free; AF) was used in the bioreactor process.

Figure 12:
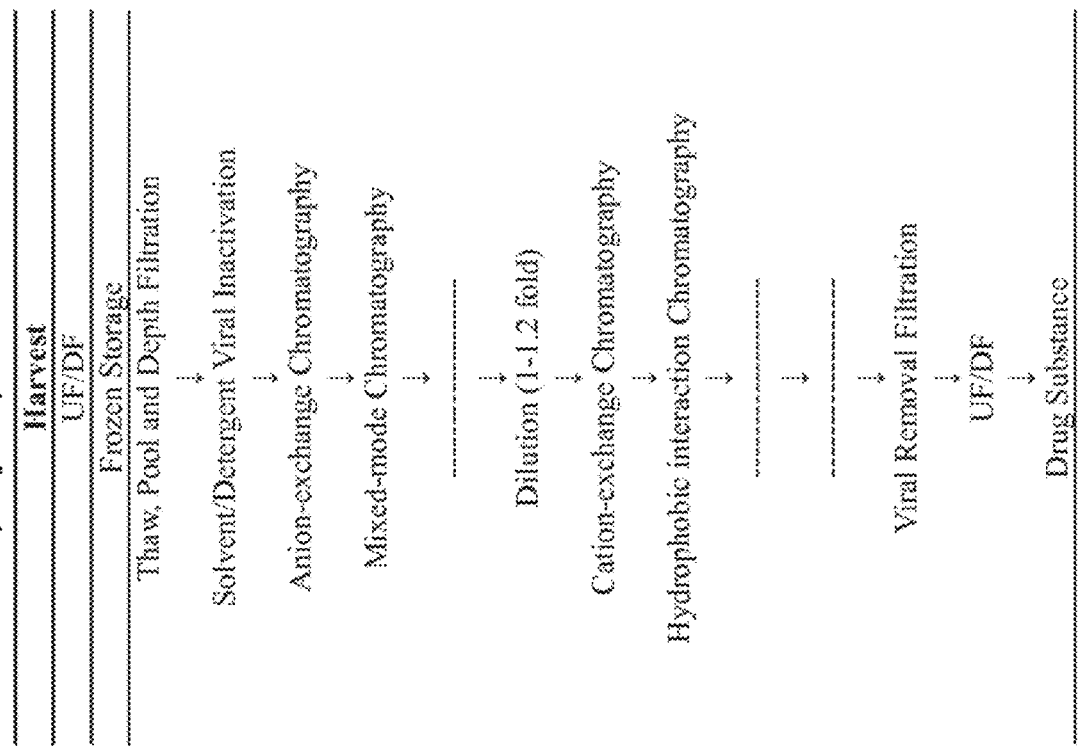
FIG. 12 depicts Table 3 which shows exemplary steps of purification process.

Individual harvest material was reduced in volume and buffer exchanged through an ultrafiltration/diafiltration process. The material, termed unpurified bulk (UPB), was frozen at −50° C. per individual harvest. The downstream purification process began with the thaw and pool of unpurified bulk and included successive viral inactivation, anion exchange (Capto Q), mixed mode (ceramic hydroxyapatite), cation exchange (SP Sepharose) and hydrophobic interaction (Phenyl Sepharose) chromatography steps followed by viral filtration, and final concentration and diafiltration step. In particular, this purification process utilized Q, hydroxyapatite, SP and Phenyl chromatographic modalities. Protein G Chromatography and Size Exclusion Chromatography traditionally used in I2S purification process were removed. Exemplary steps are shown in Table 3, as shown in FIG. 12.

Purified I2S protein were assessed for purity by peptide mapping, SDS-PAGE (Silver), size exclusion HPLC. Enzyme specific activity, formylglycine content, sialic acid content, glycan map, charge profiles were determined using standard methods. Exemplary results are shown in Table 4.

TABLE 4

Analysis of Purified Recombinant I2S Protein

| Assay | | Purified I2S (10 L scale) Min-Max (n) |
|---|---|---|
| Peptide Mapping | L1 | 100-105% (n = 3) |
| | L10 | 98-100% (n = 3) |
| | L12 | 102-102% (n = 3) |
| | L13 | 96-97% (n = 3) |
| | L14 | 102-103% (n = 3) |
| | L17 | 101-101% (n = 3) |
| | L20 | 102-103% (n = 3) |
| Host Cell Protein | | ≤62.5 (n = 5) |
| SDS-PAGE (Silver) | | Conforms |
| Ion Exchange HPLC | % Peak A | 69-69% (n = 2) |
| | % Peak B | 20-21% (n = 2) |
| | % Peak E + F | 10-11% (n = 2) |
| Size Exclusion HPLC | | 99.9-99.9% (n = 5) |
| Cellular Uptake (Bioassay) | | 85, 95% and 97% (n = 3) |
| % Formylglycine | | 87-95% (n = 5) |
| Specific Activity | | 62-78 (n = 5) |
| Glycan Map | Pk Grp 3 | 88-93% (n = 5) |
| | Pk Grp 5 | 72-110% (n = 5) |
| | Pk Grp 6 | 124-133% (n = 5) |
| | Pk Grp 7 | 78-87% (n = 5) |
| | Total Area | 94-116% (n = 5) |
| Sialic Acid | | 16-22 (n = 4) |
| Endotoxin | | <0.04-<0.05 (n = 2) |
| Bioburden | | 0.00-0.00 (n = 2) |

Figure 2:
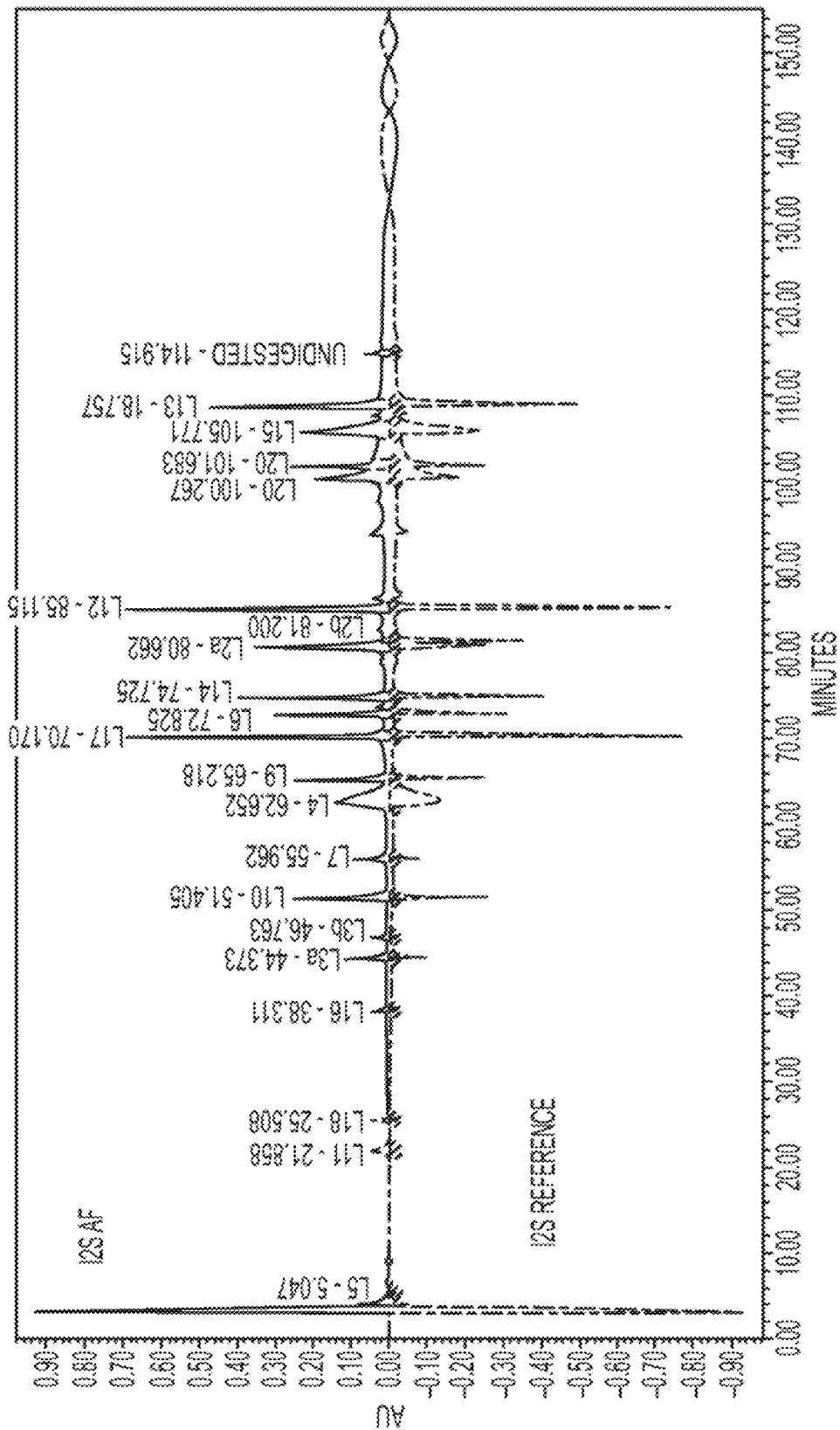
FIG. 2 depicts an exemplary peptide maps of purified recombinant I2S AF as compared to a reference I2S.
Figure 3:
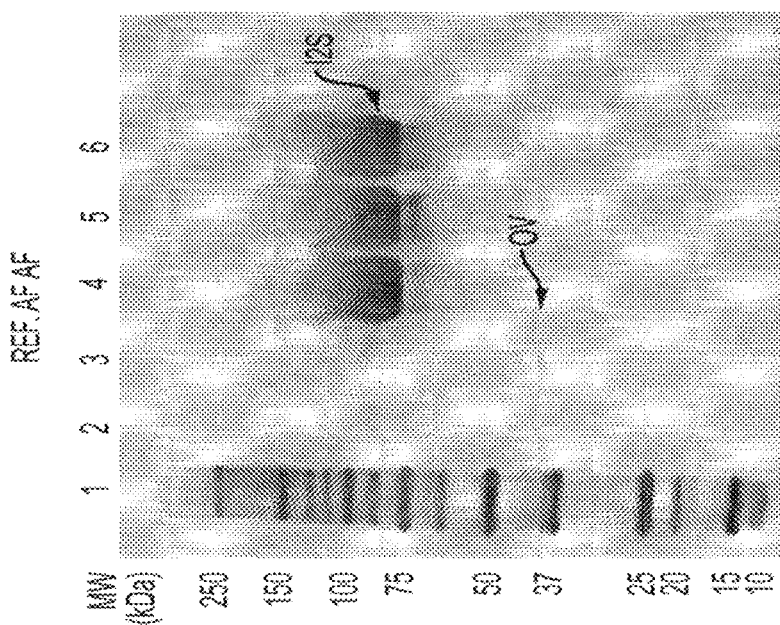
FIG. 3 depicts an exemplary SDS-PAGE (Silver) analysis of purified recombinant I2S AF.
Figure 4:
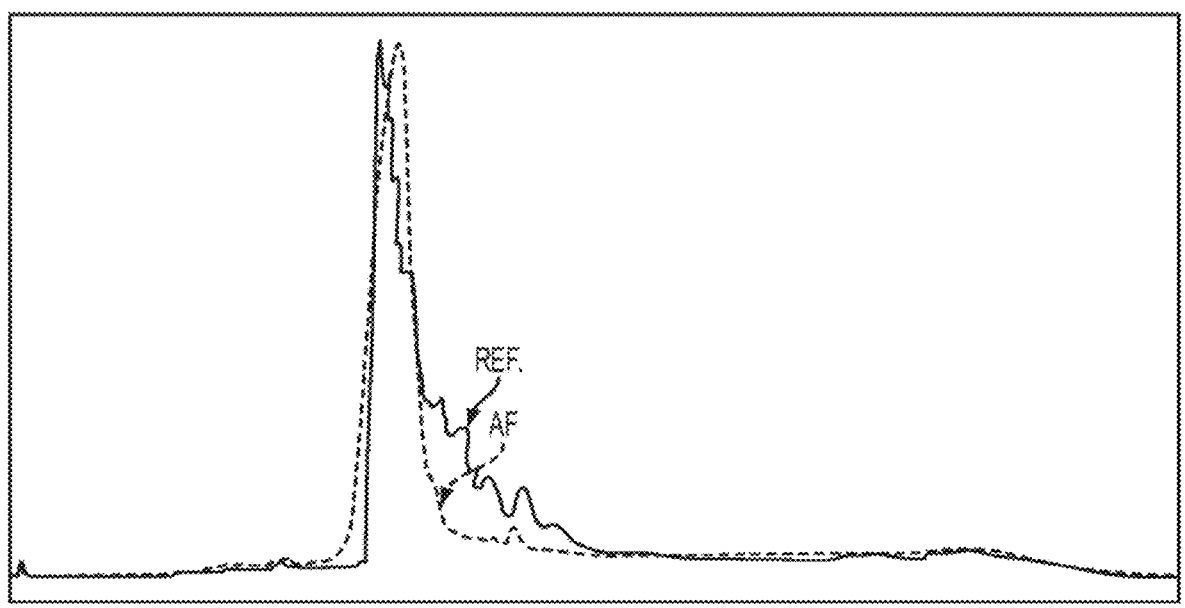
FIG. 4 depicts an exemplary charge profile analysis of purified recombinant I2S AF assessed by ion-exchange chromatography.
Figure 5:
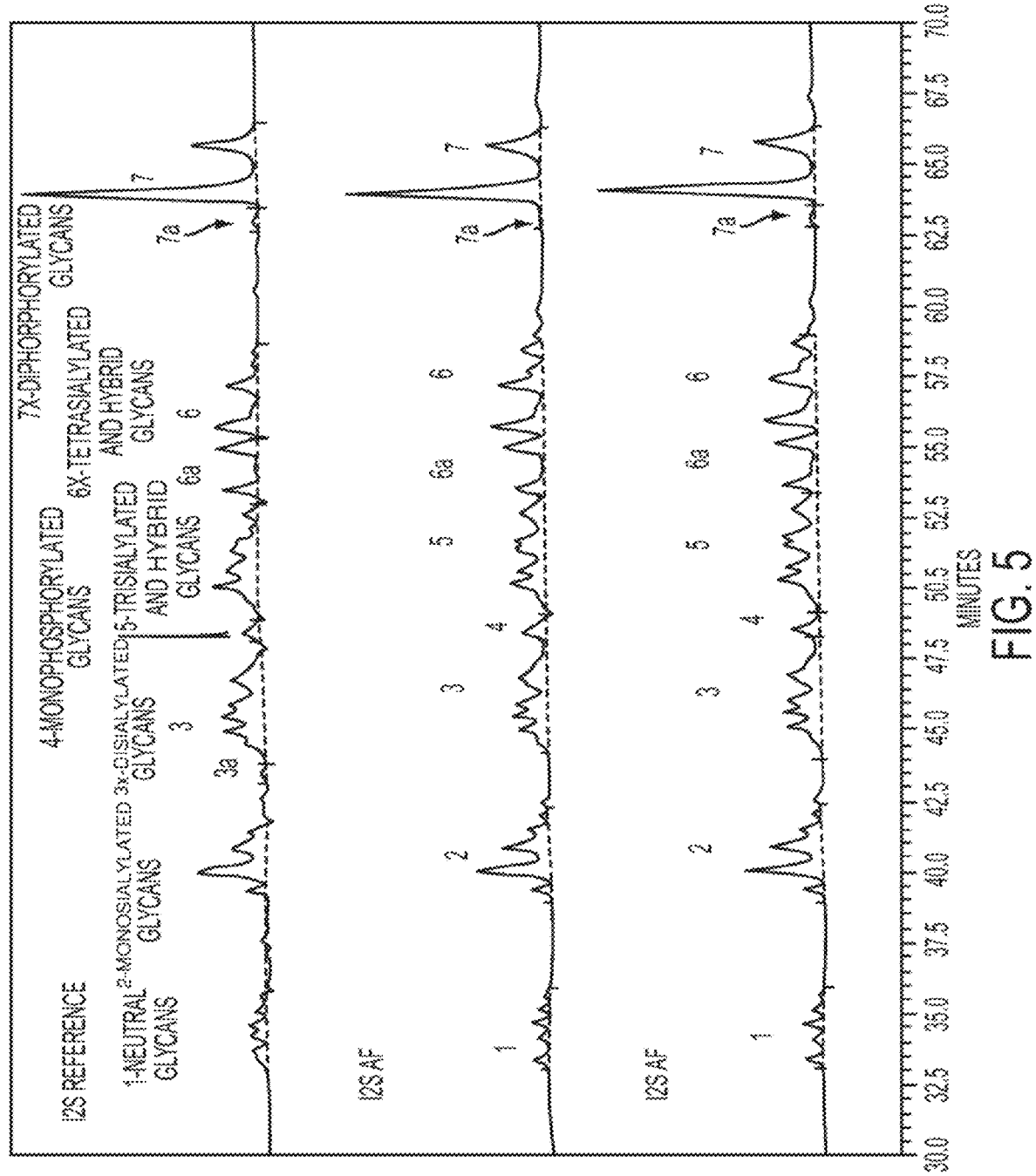
FIG. 5 depicts exemplary glycan map profiles of purified recombinant I2S AF.

An exemplary peptide map as compared to commercially available I2S reference is shown in FIG. 2. Exemplary SDS-PAGE (Silver) analysis results are shown in FIG. 3. Typically, using a process described herein, the HCP concentration of drug substance (DS) was <100 ppm, meeting the <100 ppm specification required in many markets including the US. The SEC of DS was ≥99.5%, also meeting the current >99.3% marketing specification requirement in many markets. Exemplary charge profile is shown in FIG. 4. Exemplary glycan map is shown in FIG. 5. In particular, the glycan map of purified I2S includes seven peak groups, eluting according to an increasing amount of negative charges derived from sialic acid and mannose-6-phosphate residues, representing in the order of elution, neutrals, mono-, disialylated, monophosphorylated, trisialylated and hybrid (monosialylated and capped M6P), tetrasialylated and hybrid (disialylated and capped M6P) and diphosphorylated glycans.

Taken together, this example demonstrates that a simplified four-column purification process can be used to successfully purify recombinant I2S produced in animal free medium at large scale.

Example 2: Harvest and Viral Inactivation Stability Studies of Recombinant I2S AF The objective of this study was to evaluate the effects of temperature hold time and freeze-thaw cycles on the stability of recombinant I2S clarified harvest.

Clarified harvest samples were stored at ambient and 2-8° C. for up to seven days and the viral inactivated UPB samples were held at ambient for up to 24 hours. Freeze-thaw samples on clarified harvests were frozen at −20° C., −50° C., and −80° C. and experienced freeze-thaw for up to three cycles. Stability was gauged using Western blot, SEC HPLC, and activity assay.

I2S-AF harvest material was produced from the 2D cell line by CCPD using a B. Braun 20L bioreactor with a centrifuge retention device and a desired bleeding rate. For the temperature holding study, each clarified harvest was stored at ambient and 2-8° C. and sampled at selected hold times. Sampling amounts and hold times are listed in Table 5. Freeze-thaw samples were stored at −20° C., −50° C., and −80° C. and thawed using a water bath at 25° C.

TABLE 5

Clarified Harvest Hold Point Stability

| Samples | | Holding Temperature | Holding Time (Days) |
|---|---|---|---|
| Clarified Harvest 12 | 15 × 0.5 mL | 2-8° C. | T = 0, 24 h, 76 h, 120 h, 168 h |
| | 15 × 0.5 mL | Ambient | T = 0, 24 h, 76 h, 120 h, 168 h |
| | 9 × 0.5 mL | −20° C., −50° C., and −80° C. | Freeze/Thaw 1, 2, and 3 |
| Clarified Harvest 18 | 15 × 0.5 mL | 2-8° C. | T = 0, 24 h, 76 h, 120 h, 168 h |
| | 15 × 0.5 mL | Ambient | T = 0, 24 h, 76 h, 120 h, 168 h |
| | 9 × 0.5 mL | −20° C., −50° C., and −80° C. | Freeze/Thaw 1, 2, and 3 |

The viral inactivation step occurred at the unpurified bulk step prior to loading the first column. UPB was produced by concentrating and buffer exchange of clarified harvest. UF/DF was performed using a Pall 1 sq. ft. Centramate system and buffer exchanged into 10 mM MES, 155 mM NaCl, pH=6.5. The viral inactivation step added 1% Tween 80 and 0.3% TnBP, filtered using Durapore syringe filters for each time point. Samples were taken at each time point listed in Table 6 and frozen at −80° C. Samples from the clarified harvest hold point and freeze-thaw studies were tested by Western blot and activity (4-MU assay). UPB samples from the viral inactivation were tested for purity by SEC HPLC. The hold point activity results from Harvest 12 and 18 on Table 5 showed no significant changes up to 7 days of storage at ambient and 2-8° C. for both harvests. There were no significant changes seen in Harvest 12 activity for up to 3 freeze-thaw cycles stored at −20° C., −50° C., and −80° C.

TABLE 6

Viral Inactivation of Unpurified Bulk

| | Samples | Holding Temperature | Holding Time (Days) |
|---|---|---|---|
| Viral Inactivation | 9 × 0.5 mL | Ambient, Control | T = 0, 6 h, 24 h |
| | 9 × 0.5 mL | Ambient, Viral Inactivation | T = 0, 6 h, 24 h |

Figure 6:
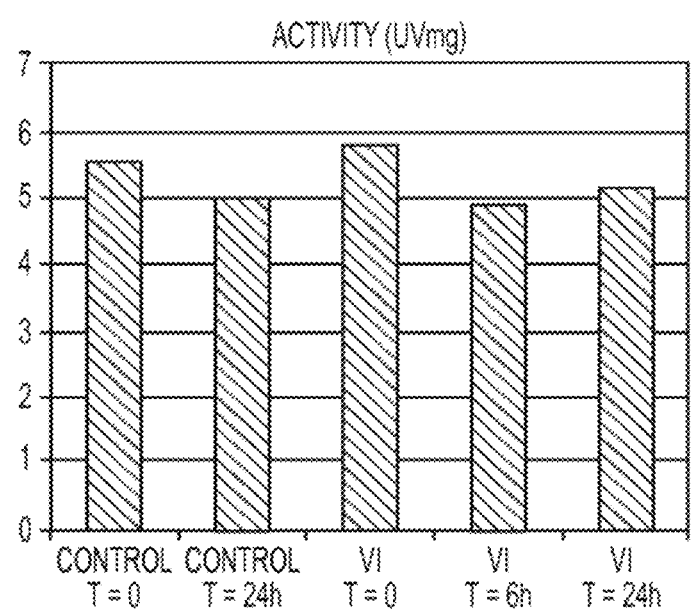
FIG. 6 depicts an exemplary analysis of activity (U/mg) after a viral inactivation UPB step of a clarified harvest of recombinant I2S.
Figure 7:
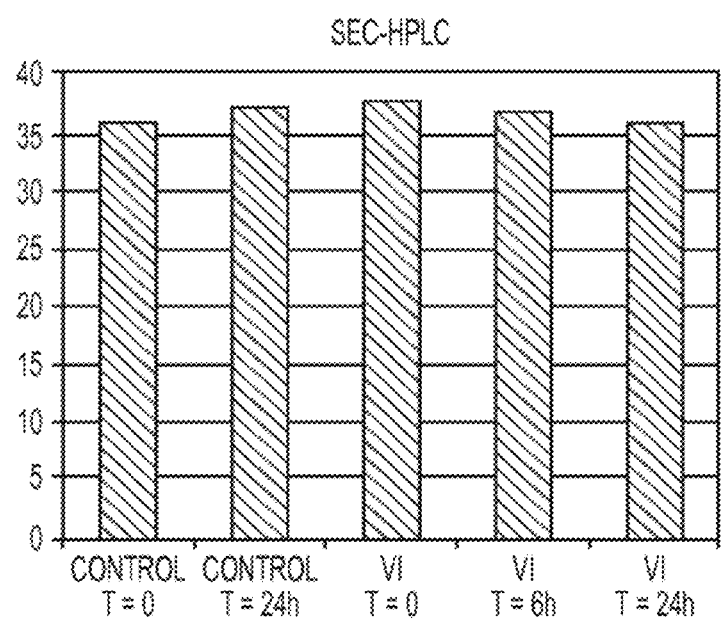
FIG. 7 depicts an exemplary analysis of SEC-HPLC after a viral inactivation UPB step of a clarified harvest of recombinant I2S.

Activity and SEC-HPLC for the stability of the viral inactivation UPB step are described in FIGS. 6 and 7. This shows that there were no issues in viral inactivation stability based on activity and purity for up to 24 hours.

In summary, based on the stability analysis described herein, clarified harvest can be stored at 2-8° C. (for example, for up to 7 days) without significant changes in harvest quality. Clarified harvests can experience multiple freeze-thaw cycles and stored at −20° C., −50° C., and −80° C. temperatures with no significant changes in stability. Based on SEC HPLC purity results, viral inactivation at the UPB step can occur at ambient temperature (e.g., for up to 24 hours) with no changes in activity and purity.

Example 3: Purification and Analysis of Animal-Free IL CD Media Confirmation Run The objective of this study was to perform purification from pooled harvest of I2S-AF produced in an animal-free perfusion using chemically defined media and to characterize the drug substance.

This study evaluated I2S-AF purification process performance and drug substance (DS) produced from a chemically defined medium bioreactor.

Cell Culture

The I2S-AF material was produced from cell line 2D expressing I2S and formylglycine generating enzyme (FGE)) as described in Example 1. The material was produced in CCPD in a 1L Das Gip spin filter bioreactor using a chemically defined serum free media. Individual bags from each clarified harvest (HI-21) were received frozen at −20° C. and thawed at 2-8° C. overnight. Equal volumes of each clarified harvest was pooled to represent an entire harvest pool, then 0.2 μm filtered and concentrated using 30 kD Pall Omega Centramate cassette with a total membrane area of 1 ft$^2$. The unpurified bulk (UPB) was 0.2 μm filtered and frozen prior to use.

Purification

Exemplary column specifications and loading are described in Table 7. The Q Sepharose was loaded at a target of 3 g/L by titer. Subsequent columns were loaded at 100% from the previous column elution and no material removed.

TABLE 7

Column and Loading Specifications

| Column | Column Dimensions (cm × cm) | Column Volume (mL) | Column Load (g/L resin by I2S) | Column Load (mg) |
|---|---|---|---|---|
| Q Sepharose | 2.6 × 25 | 133 | 3 | 399 |
| HA Type II, 80 μm | 1.6 × 30 | 60 | 5.5 | 330 |
| Phenyl Sepharose | 1.6 × 23 | 46 | 5.6 | 258 |

One purification run was performed using UPB from pooling harvests 1 through 21 from the bioreactor. UPB was thawed at 2-8° C. overnight and pooled by equal volume from each harvest.

Individual column process steps and buffer formulations can be found in Tables 8-11. The pooled UPB was filtered using a 0.2 um bottle filter system, adjusted to pH 6.5 using 1 M sodium acetate, and conductivity adjusted to 16 mS/cm with 5 M sodium chloride prior to loading onto the Q Sepharose FF column. The Q Sepharose elution was adjusted to 0.001 M NaPO$_4$ using 0.25M NaPO$_4$, pH 5.5 and filtered with a 0.22 um PES bottle top filter prior to loading onto the HA column. The HA elution conductivity was adjusted to 1.55 M NaCl with 5 M NaCl and pH adjusted to pH 5.5 with 1 M sodium acetate. The adjustment time was approximately 1 hour. The adjusted pool was filtered using a 0.22 um PES bottle top filter prior to loading onto the Phenyl Sepharose column. The Phenyl elution was concentrated 4× and diafiltered 6× into 0.02 M NaPO$_4$, 0.137 M NaCl, pH 6.0. The diafiltered product was adjusted to 2.0 g/L and formulated with 0.2% Polysorbate 20 to generate mock drug substance. A mock pool of H1-20 of the DS was created for additional characterization.

TABLE 8

Exemplary Process Details for Q Sepharose FF Chromatography

| Process Step | Flow rate (cm/hr) | CV | Buffers |
| --- | --- | --- | --- |
| Sanitization | 150 | 3 | 0.5N NaOH |
| Equilibration | 150 | 4 | 0.01M MES, 0.155M NaCl, ph 6.5 |
| Wash 1 | 150 | 2 | 0.01M MES, 0.155M NaCl, ph 6.5 |
| Wash 2 | 150 | 3 | 0.01M MES, 0.155M NaCl, ph 5.5 |
| Elution | 150 | 3 | 0.01M MES, 0.50M NaCl, ph 5.5 |
| Clean/Strip | 150 | 4 | 1.0M NaOH, 2M NaCl |
| Store | 150 | 4 | 0.0N NaOH |

TABLE 9

Exemplary Process Details for HA Chromatography

| Process Step | Flow rate (cm/hr) | CV | Buffers |
| --- | --- | --- | --- |
| Sanitization | 200 | 3 | 0.5N NaOH |
| Charge | 200 | 3 | 0.250M NaPO$_4$, pH 5.5 |
| Equilibration | 200 | 3-6 | 0.01M MES, 0.001M NaPO$_4$, 0.5M NaCl, pH 5.5 |
| Wash 1 | 200 | 1 | 0.01M MES, 0.001M NaPO$_4$, 0.5M NaCl, pH 5.5 |
| Wash 2 | 200 | 6 | 0.01M MES, 0.01M NaPO$_4$, 0.5M NaCl, pH 5.5 |
| Elution | 200 | 3 | 0.01M MES, 0.08M NaPO$_4$, pH 5.5 |
| Strip | 200 | 4 | 0.4M NaPO$_4$ pH 12 |
| Clean | 200 | 4 | 0.5N NaOH |
| Store | 200 | 4 | 0.1N NaOH |

TABLE 10

Exemplary Process Details for Phenyl Sepharose Chromatography

| Process Step | Flow rate (cm/hr) | CV | Buffers |
| --- | --- | --- | --- |
| Sanitization | 150 | 3 | 0.5N NaOH |
| Equilibration | 150 | 4-6 | 0.02M MES, 1.5M NaCl, pH 5.5 |
| Wash | 150 | 2 | 0.02M MES, 1.5M NaCl, pH 5.5 |
| Elution | 150 | 3 | 0.02M MES, 0.2M NaCl, pH 5.5 |
| Water Wash | 150 | 3 | RO/DI Water |
| Ethanol Wash | 150 | 3 | 20% Ethanol |
| Clean | 150 | 3 | 0.5N NaOH |
| Store | 150 | 3 | 0.01N NaOH |

TABLE 11

Exemplary Diafiltration of the Phenyl Elution Pool

| | |
| --- | --- |
| Filtration Unit | Centricon Plus 70 |
| Diafiltration Buffer | 0.02M NaPO$_4$, 0.137M NaCl, pH 6.0 |
| Diafiltration Volumes | 6 X-8 X |

In Process Purity by HCP by ELISA

Table 12 describes the in-process HOP removal for each step. The in-process HCP results were high with the majority of removal at the HA step.

TABLE 12

In-Process HCP Removal

| Step | HCP (ng/mg) | LRV | HCP Fold |
| --- | --- | --- | --- |
| Q | 46,392 | 0.3 | 2 |
| | 51,957 | | |
| HA | 51,957 | 1.3 | 18 |
| | 5,876 | | |
| Phenyl | 5,876 | 0.7 | 5 |
| | 1,870 | | |

Drug Substance Characterization

Exemplary drug substance lot release results are listed in Table 13. As can be seen, the drug substance had high specific activity and % FG in the purified material. Exemplary drug attributes characterization is shown in Table 13. HCP was reduced from 1,870 ng/mg to 372 ng/mg at the final UF/DF step.

TABLE 13

Exemplary Drug Substance Lot Release

| DS Lot Release | 1L CD media (I2S-AF) |
| --- | --- |
| % FG | 94% |
| Glycan Map | |
| Group 3 | 99% |
| Group 5 | 89% |
| Group 6 | 104% |
| Group 7 (2-M6P) | 95% |
| Total Area | 107% |
| Sialic Acid | 17 |
| Internalization | 83% |
| SEC-HPLC | 99.9% |
| Specific Activity (U/mg) | 82 |
| IEX HPLC | |
| A (%) | 64% |
| B (%) | 23% |
| A + B | 87% |
| E + F | 0% |
| Host Cell Protein | 372 |
| Cell Uptake | 98 |

Example 4. Physiochemical and Biological Characterization of Purified Recombinant I2S Enzyme The purpose of the example was to perform a detailed characterization of the recombinant I2S protein purified using methods described above.

SDS-PAGE

Figure 8:
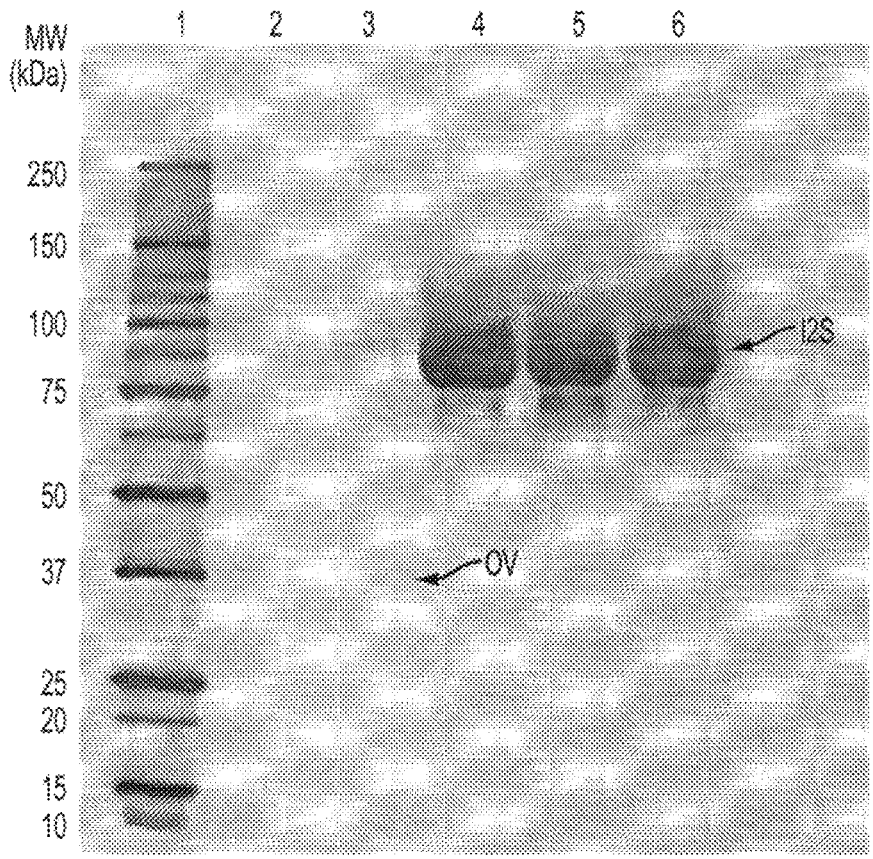
FIG. 8 depicts exemplary SDS-PAGE treated with silver stain of purified recombinant I2S protein.

For the experiment, recombinant I2S protein was generated using the 2D and 4D human cell lines, in two separate serum-free cell culture reactions. Samples were collected and purified using methods described above. Purified I2S enzyme was analyzed by SDS-PAGE, and treated with silver stain for visualization. Exemplary results are shown in FIG. 8. As can be seen from FIG. 8, purified recombinant I2S protein using methods described herein present comparable banding patterns as compared to the I2S reference sample purified using standard method.

Peptide Map

Figure 9:
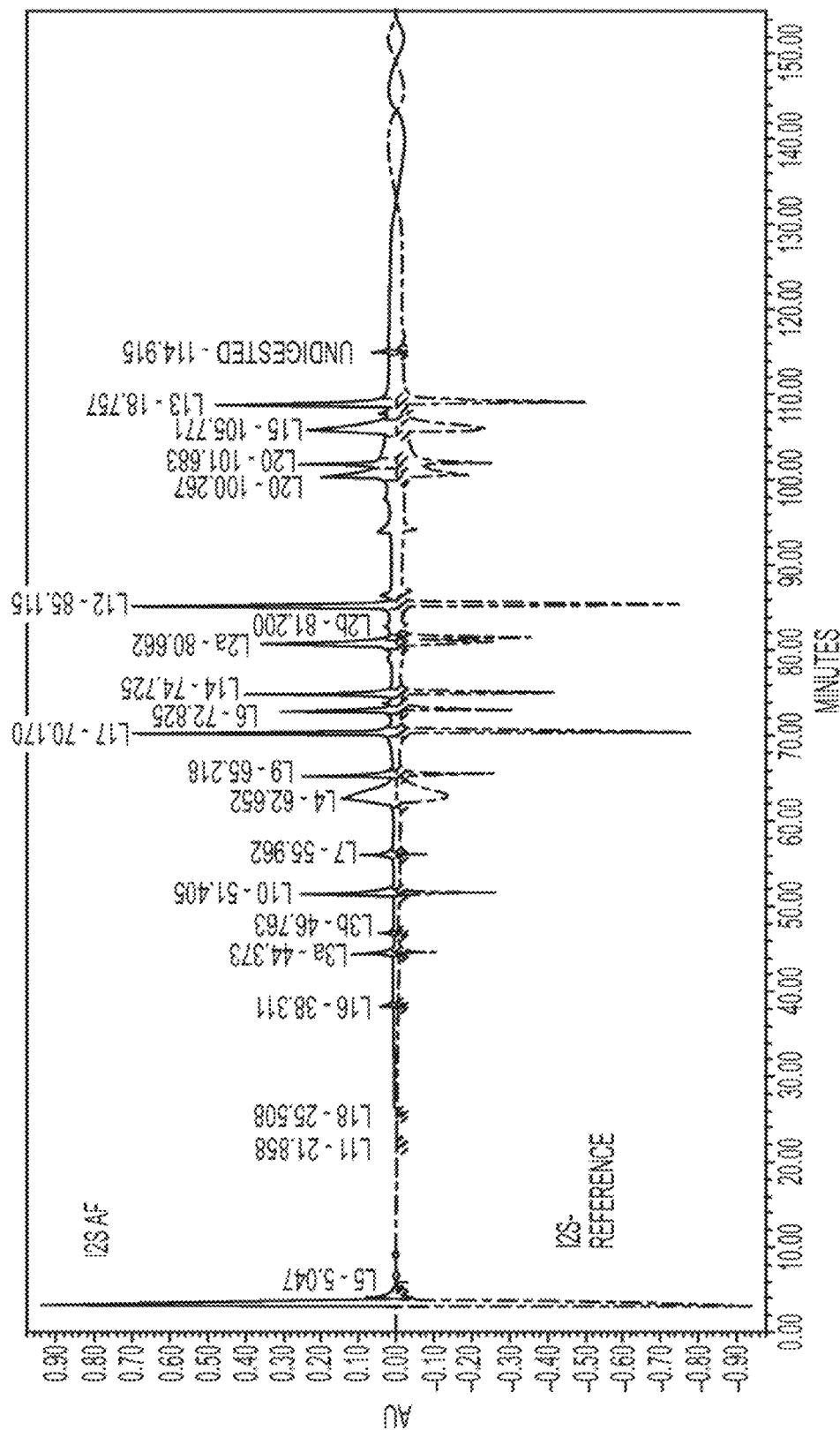
FIG. 9 shows an exemplary peptide map for a purified recombinant I2S enzyme produced from the I2S-AF 2D cell line grown under serum-free culture conditions (top panel) as compared to a reference.

Recombinant I2S protein produced by the I2S-AF 2D cell line was purified using methods as described above. Purified recombinant I2S and a sample of reference human I2S were each subjected to proteolytic digest and examined by HPLC analysis. An exemplary peptide map as compared to that of a reference I2S is shown in FIG. 9.

Percent Formylglycine Conversion

Peptide mapping can be used to determine Percent FGly conversion. I2S activation requires Cysteine (corresponding to position 59 of the mature human I2S) to formylglycine conversion by formylglycine generating enzyme (FGE) as shown below:

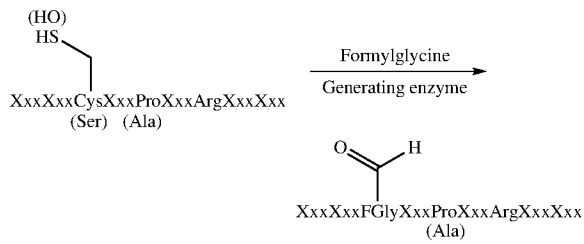

Therefore, the percentage of formylglycine conversion (% FG) can be calculated using the following formula:

$$\% FG \text{ (of } DS\text{)} = \frac{\text{Number of active } I2S \text{ molecules}}{\text{Number of total (active + inactive) } I2S \text{ molecules}} \times 100$$

For example 50% FG means half of the purified recombinant I2S is enzymatically inactive without any therapeutic effect.

Peptide mapping was used to calculate % FG. Briefly, a purified recombinant I2S protein was digested into short peptides using a protease (e.g., trypsin or chymotrypsin). Short peptides were separated and characterized using HPLC. The peptide containing the position corresponding to position 59 of the mature human I2S was characterized to determine if the Cys at position 59 was converted to a FGly as compared to a control (e.g., an I2S protein without FGly conversion or an I2S protein with 100% FGly conversion). The amount of peptides containing FGly (corresponding to number of active I2S molecules) and the total amount of peptides with both FGly and Cys (corresponding to number of total I2S molecules) may be determined based on the corresponding peak areas and the ratio reflecting % FG was calculated. Exemplary results are shown in Table 14.

Glycan Map-Mannose-6-Phosphate and Sialic Acid Content

The glycan and sialic acid composition of purified recombinant I2S protein was determined. Quantification of the glycan composition was performed, using anion exchange chromatography to produce a glycan map. As described below, the glycan map of recombinant I2S purified under conditions described herein consists of seven peak groups, eluting according to an increasing amount of negative charges, at least partly derived from sialic acid and mannose-6-phosphate glycoforms resulting from enzymatic digest. Briefly, purified recombinant I2S from the serum-free cell culture (I2S-AF 2D Serum-free and I2S-AF 4D Serum-free) and reference recombinant I2S, were treated with either (1) purified neuraminidase enzyme (isolated from *Arthrobacter Ureafaciens* (10 mU/uL), Roche Biochemical (Indianapolis, IN), Cat. #269 611 (1U/100 uL)) for the removal of sialic acid residues, (2)alkaline phosphatase for 2 hours at 37±1° C. for complete release of mannose-6-phosphate residues, (3)alkaline phosphatase+neuraminidase, or (4) no treatment. Each enzymatic digest was analyzed by High Performance Anion Exchange Chromatography with Pulsed Amperometric Detection (HPAE-PAD) using a CarboPac PAI Analytical Column equipped with a Dionex CarboPac PAI Guard Column. A series of sialic acid and mannose-6-phosphate standards in the range of 0.4 to 2.0 nmoles were run for each assay. An isocratic method using 48 mM sodium acetate in 100 mM sodium hydroxide was run for a minimum of 15 minutes at a flow rate of 1.0 mL/min at ambient column temperature to elute each peak. The data generated from each individual run, for both the I2S-AF and reference I2S samples, were each combined into a single chromatograph to represent the glycan map for each respective recombinant protein. As indicated in FIG. 10, the glycan map for I2S purified from serum-free medium showed representative elution peaks (in the order of elution) constituting neutrals, mono-, disialyated, monophosphorylated, trisialyated and hybrid (monosialyated and capped mannose-6-phosphate), tetra-sialylated and hybrid (disilaylated and capped mannose-6-phosphate) and diphosphorylated glycans. Exemplary glycan mapsa are shown in FIG. 10.

Average sialic acid content (moles sialic acid per mole protein) in each recombinant I2S sample was calculated from linear regression analysis of sialic acid standards. Each chromatogram run was visualized using the PeakNet 6 Software. Sialic acid standards and sialic acid released from recombinant I2S assay control and test samples appear as a single peak. The amount of sialic acid (nmoles) for I2S was calculated as a raw value using the following equation:

$$S.A.\text{(mole per mole } I2S\text{)} = \frac{(nmoles \text{ sialic acid})}{(0.3272)(C)}$$

Where C is the protein concentration (in mg/ml) of sample or recombinant I2S assay control. The corrected value of sialic acid as moles of sialic acid per mole of protein for each test sample was calculated using the following formula:

$$\text{Corrected } S.A. = \frac{\begin{array}{c}(\text{Sample Raw Sialic Acid Value}) \times \\ (\text{Established Idursulfase Assay Control Value})\end{array}}{(\text{Idursulfase Assay Control Raw Sialic Acid Value})}$$

Exemplary data indicative of sialic acid content on the recombinant I2S purified from I2S-AF 2D or 4D cell lines are shown in Table 14.

TABLE 14

Exemplary Characteristics of I2S Purified from Serum-Free Cell Culture

| Assay | I2S-AF 2D (Serum-free) |
|---|---|
| Peptide Mapping | |
| L1 | 101 |
| L10 | 100 |
| L12 | 102 |
| L13 | 97 |
| L14 | 101 |
| L17 | 100 |
| L20 | 102 |
| Host Cell Protein | <62.5 ng/mg |
| Ion Exchange HPLC % Area | |
| Peak A | 62 |
| Peak A + B | 82 |
| Peak E + F | 0 |
| % Formylglycine | 87 |
| Specific activity (U/mg) (sulfate release assay) | 64 |
| % Size Exclusion HPLC | ≥99.8 (n = 13) |
| Glycan Mapping | |
| Monosialylated | 105 |
| Disialylated | 93 |
| Monophosphorylated | 139 |
| Trisialylated | 89 |
| Tetrasialylated | 125 |
| Diphosphorylated | 95 |
| Sialic Acid (mol/mol) | 20 |

Specific Activity

Specific activity of the recombinant I2S enzyme purified using methods described herein was analyzed using in vitro sulfate release assay or 4-MUF assay.

In Vitro Sulfate Release Assay

In vitro sulfate release activity assay was conducted using heparin disaccharide as substrate. In particular, this assay measures the ability of I2S to release sulfate ions from a naturally derived substrate, heparin diasaccharide. The released sulfate may be quantified by ion chromatography equipped with a conductivity detector. Briefly, samples were first buffer exchanged to 10 mM Na acetate, pH 6 to remove inhibition by phosphate ions in the formulation buffer. Samples were then diluted to 0.075 mg/ml with reaction buffer (10 mM Na acetate, pH 4.4) and incubated for 2 hrs at 37° C. with heparin disaccharide at an enzyme to substrate ratio of 0.3 μg I2S/100 μg substrate in a 30 μL reaction volume. The reaction was then stopped by heating the samples at 100° C. for 3 min. The analysis was carried out using a Dionex IonPac AS18 analytical column with an IonPac AG18 guard column. An isocratic method was used with 30 mM potassium hydroxide at 1.0 ml/min for 15 minutes. The amount of sulfate released by the I2S sample was calculated from the linear regression analysis of sulfate standards in the range of 1.7 to 16.0 nmoles. The reportable value was expressed as Units per mg protein, where 1 unit is defined as 1 μmoles of sulfate released per hour and the protein concentration is determined by A280 measurements. Exemplary results are shown in Table 14.

4-MUF Assay

Specific activity of the purified recombinant I2S enzyme may also be analyzed using the fluorescence based 4-MUF assay. Briefly, the assay measures the hydrolysis of I2S substrate 4-methylumbelliferyl-sulfate (4-MUF-SO$_4$). Upon cleavage of the 4-MUF-SO$_4$ substrate by I2S, the molecule is converted to sulfate and naturally fluorescent 4-methylumbelliferone (4-MUF). As a result, I2S enzyme activity can be determined by evaluating the overall change in fluorescent signal over time. For this experiment, purified I2S enzyme were incubated with a solution of 4-methylumbelliferyl-sulfate (4-MUF-SO$_4$), Potassium Salt, Sigma Cat. #M-7133). Calibration of the assay was performed using a series of control reference samples, using commercially available I2S enzyme diluted at 1:100, 1:200 and 1:20,000 of the stock solution. The enzymatic assay was run at 37° C. and assayed using a calibrated fluorometer. Using the fluorescence values obtained for each reference standard, the percent coefficient of variation was determined using the following equation:

$$\%CV = \frac{S\tan dard \text{ Deviation of Raw Fluorescenc Values}(N=3)}{Averagel \text{ Fluorescence Value}} \times 100\%$$

The percent CV values were then used to calculate the Corrected Average Fluorescence for each sample, in order to determine the reportable enzyme activity, expressed in mU/mL using the following formula:

$$mU/mL = (CFU)\left(\frac{1\,nmole/L}{10\,FU}\right)\left(\frac{1L}{10^3\,mL}\right)\left(\frac{2.11\,mL}{0.01\,mL}\right)\left(\frac{1\,hour}{60\,min}\right)\left(\frac{1\,mU}{nmole}\right)(DF)$$

CFU=Negative corrected average fluorescence

DF-Dilution Factor

One milliunit of activity is the quantity of enzyme required to convert 1 nanomole of 4-methylumbelliferyl-sulfate to 4-methylumbelliferone in 1 minute at 37° C.

Charge Profile

For this experiment, the charge distribution of each purified recombinant I2S was determined by Strong Anion Exchange (SAX) Chromatography, with a High Performance Liquid Chromatography (HPLC) system. The method separates recombinant I2S variants within the sample, based on surface charge differences. At pH 8.00, negatively charged species adsorb onto the fixed positive charge of the SAX column. A gradient of increasing ionic strength is used to elute each protein species in proportion to the strength of their ionic interaction with the column. One hundred micrograms of purified I2S, isolated from the 2D cell line under serum-free growth conditions or reference recombinant I2S enzyme, was loaded onto an Amersham Biosciences Mini Q PE (4.6×50 mm) column held at ambient temperature and equilibrated to 20 mM Tris-HCl, pH 8.00. Gradient elution was made at a flow rate of 0.80 mL/min, using a mobile phase of 20 mM Tris-HCl, 1.0 M sodium chloride, pH 8.00. Protein concentration was continuously determined during the run, by measuring light absorbance of the sample elution at the 280 nm wavelength. Exemplary results showing charge profiles observed for recombinant I2S purified from 2D and 4D cell lines are shown in FIG. 11.

What is claimed is:

1. A method of treating Hunter syndrome comprising administering to a subject in need of treatment a composition comprising purified recombinant iduronate-2-sulfatase (I2S) having an amino acid sequence with at least 95% sequence identity to SEQ ID NO: 1 and a carrier, wherein the purified recombinant I2S comprises at least 70% conversion of the cysteine residue corresponding to Cys59 of SEQ ID NO:1 to Cα-formylglycine (FGly), and wherein the purified recombinant I2S contains less than 150 ng Host Cell Protein (HCP)/mg I2S.

2. The method of claim 1, wherein the purified recombinant I2S comprises at least 75% conversion of the cysteine residue corresponding to Cys59 of SEQ ID NO: 1 to Cα-formylglycine (FGly).

3. The method of claim 1, wherein the purified recombinant I2S comprises at least 85% conversion of the cysteine residue corresponding to Cys59 of SEQ ID NO: 1 to Cα-formylglycine (FGly).

4. The method of claim 1, wherein the purified recombinant I2S comprises a moiety that binds to a receptor on the surface of target cells.

5. The method of claim 4, wherein the moiety is fused to the I2S protein at the N-terminus, C-terminus or internally.

6. The method of claim 1, wherein the composition is administered by intrathecal or intravenous administration.

7. The method of claim 6, wherein the composition is administered by intrathecal administration.

8. The method of claim 6, wherein the composition is administered by intravenous administration.

9. The method of claim 1, wherein the composition is administered once weekly.

10. The method of claim 1, wherein the composition is administered biweekly.

11. The method of claim 1, wherein the composition is administered once monthly.

12. The method of claim 1, wherein administration of the composition results in a reduction of zebra bodies in the patient.

13. The method of claim 1, wherein administration of the composition results in a reduction in the amount of glycosaminoglycans within lysosomes of the patient.

* * * * *

SEQUENCE LISTING

```
Sequence total quantity: 4
SEQ ID NO: 1           moltype = AA  length = 525
FEATURE                Location/Qualifiers
source                 1..525
                       mol_type = protein
                       organism = Homo sapiens
SEQUENCE: 1
SETQANSTTD ALNVLLIIVD DLRPSLGCYG DKLVRSPNID QLASHSLLFQ NAFAQQAVCA    60
PSRVSFLTGR RPDTTRLYDF NSYWRVHAGN FSTIPQYFKE NGYVTMSVGK VFHPGISSNH   120
TDDSPYSWSF PPYHPSSEKY ENTKTCRGPD GELHANLLCP VDVLDVPEGT LPDKQSTEQA   180
IQLLEKMKTS ASPFFLAVGY HKPHIPFRYP KEFQKLYPLE NITLAPDPEV PDGLPPVAYN   240
PWMDIRQRED VQALNISVPY GPIPVDFQRK IRQSYFASVS YLDTQVGRLL SALDDLQLAN   300
STIIAFTSDH GWALGEHGEW AKYSNFDVAT HVPLIFYVPG RTASLPEAGE KLFPYLDPFD   360
SASQLMEPGR QSMDLVELVS LFPTLAGLAG LQVPPRCPVP SFHVELCREG KNLLKHFRFR   420
DLEEDPYLPG NPRELIAYSQ YPRPSDIPQW NSDKPSLKDI KIMGYSIRTI DYRYTVWVGF   480
NPDEFLANFS DIHAGELYFV DSDPLQDHNM YNDSQGGDLF QLLMP                   525

SEQ ID NO: 2           moltype = AA  length = 550
FEATURE                Location/Qualifiers
source                 1..550
                       mol_type = protein
                       organism = Homo sapiens
SEQUENCE: 2
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLI   360
FYVPGRTASL PEAGEKLFPY LDPFDSASQL MEPGRQSMDL VELVSLFPTL AGLAGLQVPP   420
RCPVPSFHVE LCREGKNLLK HFRFRDLEED PYLPGNPREL IAYSQYPRPS DIPQWNSDKP   480
SLKDIKIMGY SIRTIDYRYT VWVGFNPDEF LANFSDIHAG ELYFVDSDPL QDHNMYNDSQ   540
GGDLFQLLMP                                                         550

SEQ ID NO: 3           moltype = AA  length = 312
FEATURE                Location/Qualifiers
source                 1..312
                       mol_type = protein
                       organism = Homo sapiens
SEQUENCE: 3
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQEDQSSTG   300
FRLKTSSTRK YK                                                      312

SEQ ID NO: 4           moltype = AA  length = 343
FEATURE                Location/Qualifiers
source                 1..343
                       mol_type = protein
                       organism = Homo sapiens
SEQUENCE: 4
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGFLMR TNT                     343
```